US011421025B2

(12) United States Patent
Koriyama et al.

(10) Patent No.: US 11,421,025 B2
(45) Date of Patent: Aug. 23, 2022

(54) TREATMENT OF IL-17A DISEASES

(71) Applicant: OSAKA UNIVERSITY, Suita (JP)

(72) Inventors: Hiroshi Koriyama, Suita (JP);
Hironori Nakagami, Suita (JP);
Ryuichi Morishita, Suita (JP)

(73) Assignee: OSAKA UNIVERSITY, Suita (JP)

( * ) Notice: Subject to any disclaimer, the term of this patent is extended or adjusted under 35 U.S.C. 154(b) by 273 days.

(21) Appl. No.: 15/108,415

(22) PCT Filed: Dec. 26, 2014

(86) PCT No.: PCT/JP2014/084682
§ 371 (c)(1),
(2) Date: Jun. 27, 2016

(87) PCT Pub. No.: WO2015/099167
PCT Pub. Date: Jul. 2, 2015

(65) Prior Publication Data
US 2016/0319013 A1    Nov. 3, 2016

(30) Foreign Application Priority Data

Dec. 27, 2013   (JP) .............................. JP2013-273133

(51) Int. Cl.
*A61K 39/00*   (2006.01)
*C07K 16/24*   (2006.01)

(52) U.S. Cl.
CPC ........ *C07K 16/244* (2013.01); *A61K 39/0005* (2013.01); *C07K 2317/34* (2013.01); *C07K 2317/76* (2013.01)

(58) Field of Classification Search
CPC .............. C07K 16/244; C07K 2317/34; C07K 2317/76
See application file for complete search history.

(56) References Cited

U.S. PATENT DOCUMENTS

| 2007/0218062 | A1 | 9/2007 | Irving |
| 2011/0027290 | A1* | 2/2011 | Allan .................... C07K 16/244 424/145.1 |
| 2013/0202610 | A1 | 8/2013 | Guettner et al. |
| 2014/0099335 | A1 | 4/2014 | Morishita et al. |
| 2019/0105388 | A1 | 4/2019 | Nakagami et al. |

FOREIGN PATENT DOCUMENTS

WO    WO 2007/070750 A1    6/2007

OTHER PUBLICATIONS

E. Benjamin et al., "Antigenicity". Immunology, A Short Course, 2nd ed., 1992 (John Wiley & Sons, Inc.), p. 40.*
Ambrosi et al., "IL-17: A new actor in IFN-driven systemic autoimmune diseases," *European Journal of Immunology*, 42(9): 2274-2284 (2012).
Crispín et al., "Protein phosphatase 2A confers susceptibility to autoimmune disease through an IL-17-dependent mechanism," *Journal of Immunology*, 188(8): 3567-3571 (2012).
Doreau et al., "Interleukin 17 acts in synergy with B cell-activating factor to influence B cell biology and the pathophysiology of systemic lupus erythematosus," *Nature Immunology*, 10(7): 778-785 (2009).
Guan et al., "An IL-17 peptide-based and virus-like particle vaccine enhances the bioactivity of IL-17 in vitro and in vivo," *Immunotherapy*, 4(12): 1799-1807 (2012).
Ma et al., "Targeting TGF-β1 by Employing a Vaccine Ameliorates Fibrosis in a Mouse Model of Chronic Colitis," *Inflammatory Bowel Diseases*, 16(6): 1040-1050 (2010).
Ohtsuki et al., "Secukinumab efficacy and safety in Japanese patients with moderate-to-severe plaque psoriasis: Subanalysis from ERASURE, a randomized, placebo-controlled, phase 3 study," *Journal of Dermatology*, 41(12): 1039-1046 (2014).
Röhn et al., "Vaccination against IL-17 suppresses autoimmune arthritis and encephalomyelitis," *European Journal of Immunology*, 36(11): 2857-2867 (2006).
Japanese Patent Office, International Search Report in International Patent Application No. PCT/JP2014/084682 (dated Apr. 7, 2015).
Novartis Pharmaceuticals, "View of NCT01365455 on Oct. 15, 2013," *ClinicalTrials.gov Archive* (2013) [obtained at https://clinicaltrials.gov/archive/NCT01365455/2013_10_15 on Jun. 27, 2017].
Jin et al., "IL-17/IFN-γInteractions Regulate Intestinal Inflammation in TNBS-Induced Acute Colitis," *J. Interferon Cytokine Res.*, 32(11): 548-556 (2012).
Sonderegger et al., "Neutralization of IL-17 by active vaccination inhibits IL-23-dependent autoimmune myocarditis," *Eur. J. Immunol.*, 36(11): 2849-2856 (2006).
Uyttenhove et al., "Development of an anti-IL-17A auto-vaccine that prevents experimental auto-immune encephalomyelitis," *Eur. J. Immunol.*, 36(11): 2868-2874 (2006).

* cited by examiner

*Primary Examiner* — Dong Jiang
(74) *Attorney, Agent, or Firm* — Leydig, Voit & Mayer, Ltd.

(57) ABSTRACT

The present invention provides a vaccine against IL-17A, which uses, as an immunogen, a polypeptide containing the amino acid sequence shown in SEQ ID NO: 1, or an amino acid sequence derived from a non-human mammal, which corresponds to SEQ ID NO: 1, a prophylactic or therapeutic agent containing the vaccine for diseases involving IL-17A as an aggravation factor, and the like.

19 Claims, 21 Drawing Sheets
Specification includes a Sequence Listing.

A

B

A

NZBWF1 31-week-old

HBc-IL-17A1 n=6
HBc n=6
Saline n=6

B

NZBWF1 41-week-old

HBc-IL-17A1 n=4
Saline n=3

Fig. 6-2
C
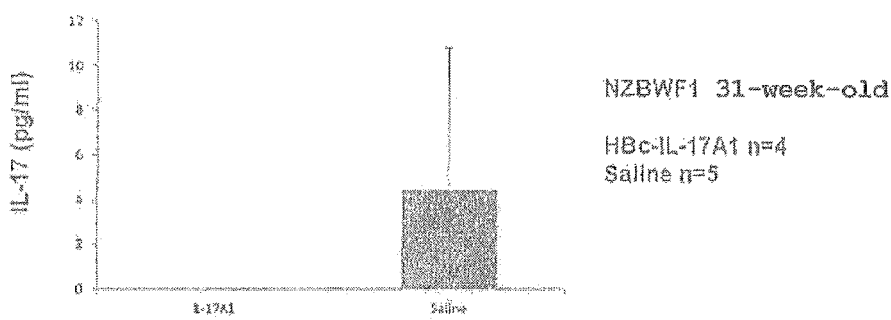
NZBWF1 31-week-old
HBc-IL-17A1 n=4
Saline n=5
D
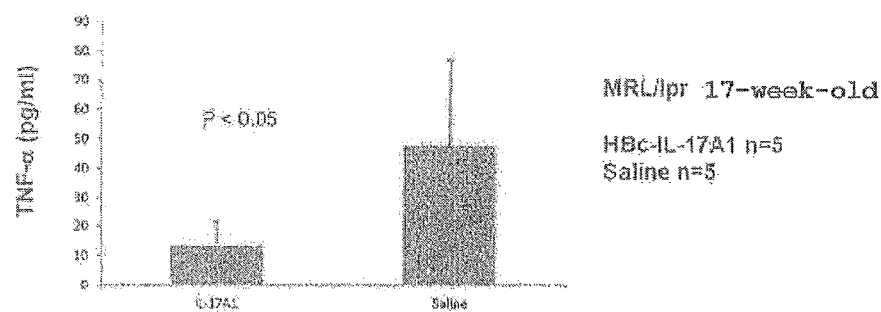
MRL/lpr 17-week-old
HBc-IL-17A1 n=5
Saline n=5
E
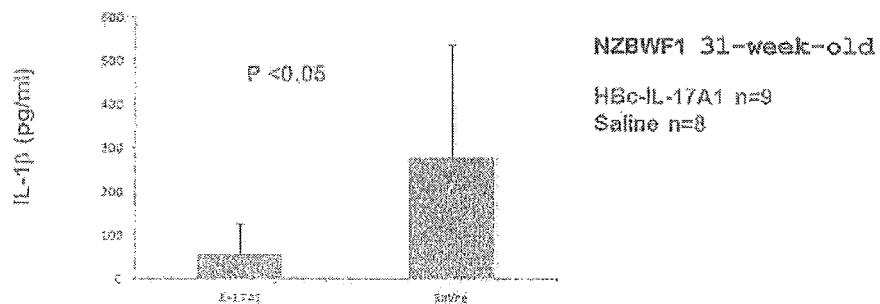
NZBWF1 31-week-old
HBc-IL-17A1 n=9
Saline n=8
F
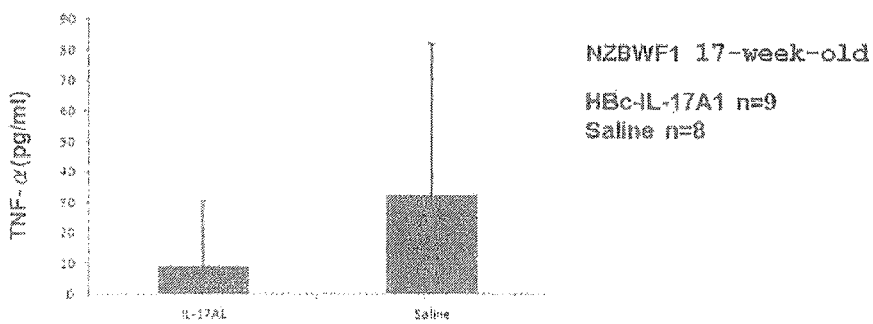
NZBWF1 17-week-old
HBc-IL-17A1 n=9
Saline n=8

A

B

A

- Divide NZBWF1 into three groups
HBc-IL-17 group (n=9), Saline group (n=9)

- Inject 30μg/30μl DNA vaccine × 2 sites × 3 times
by 30G needle with electroporation

B

- Divide MRL/lpr into two groups
HBc-IL-17 group (n=9), Saline group (n=9)

- Inject 30μg/30μl DNA vaccine × 2 sites × 3 times
by 30G needle with electroporation

A

17A1      PAS staining NZBWF1 destruction of glomerulus, stroma was     Saline   PAS staining
suppressed in vaccine group                                NZBWF1

C infiltration of macrophage was suppressed in vaccine group

F4/80 immunostaining NZBWF1

D infiltration of macrophage was suppressed in vaccine group

F4/80 immunostaining MRL/lpr

HE staining of submandibular gland

17A1

Saline inflammatory cell infiltration (submandibular gland inflammation) was suppressed in vaccine group HE staining NZBWF1
submandibular gland

A

No specific view such as inflammatory cell
infiltration etc. in both groups     HE staining NZBWF1 Liver

B

No specific view such as inflammatory cell
infiltration etc. in both groups     HE staining MRL/lpr Liver

TREATMENT OF IL-17A DISEASES

CROSS-REFERENCE TO RELATED APPLICATIONS

This patent application is the U.S. national phase of International Patent Application No. PCT/JP2014/084682, filed Dec. 26, 2014, which claims the benefit of Japanese Patent Application No. 2013-273133, filed on Dec. 27, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,605 bytes ASCII (Text) file named "725797SequenceListing.txt," created Jun. 23, 2016.

TECHNICAL FIELD

The present invention relates to a vaccine targeting an IL-17A epitope and the like.

BACKGROUND ART

Systemic lupus erythematosus (SLE) is an autoimmune disease that affects every part of the body from scalp to toe, and is a chronic inflammatory disease that has various symptoms and affects many organs. As the pathology of SLE, a vicious circle in which an immune complex of autoantigen and antibody is deposited in each organ to induce topical inflammation, which causes tissue disorder to trigger a further autoimmune reaction, and involvement of cytokines such as type I interferon and the like during the process thereof are assumed. However, the detail is unknown.

Since many of the SLE patients are females of childbearing age, the relationship between female hormone and the etiology is suspected. On the other hand, since SLE is prevalent in black woman than white woman in North America, the presence of genetic factor is suspected. However, the etiology is still unknown.

SLE is treated with adrenal cortical steroid, immunosuppressant, cyclophosphamide as anticancer agent and the like, and a non-specific immunosuppressive action can suppress the disease state of SLE. On the other hand, the non-specific immunosuppressive action causes problems such as easy affection with infections and the like. Moreover, adrenal cortical steroid causes side effects such as hypertension, diabetes, hyperlipemia, depression and the like, and cyclophosphamide is associated with strong side effects of myelosuppression, carcinogenesis, and infertility. Since many of the SLE patients are female of childbearing age, the problem of infertility is particularly serious.

As the situation stands, more detailed elucidation of the pathology and the development of a molecule-specific treatment method based on the etiology thereof and causing less side effects have been desired.

From clinical studies of SLE patients, it has been reported in recent years that the blood IL-17 concentration of SLE patients is significantly higher than that of the control group (non-patent document 1). In PP2A transgenic mouse having a lesion similar to SLE in the kidney, moreover, an increase in the blood concentration of IL-17, and improvement of kidney lesion by the administration of a neutralizing antibody to IL-17 to the mouse have been reported (non-patent document 2). From these findings, a hypothesis has been proposed as one possibility that, in the pathology of SLE, type I interferon and IL-17 form a vicious circle, and play an important role in the progress of the lesion (non-patent document 3).

IL-17 is a cytokine secreted by immunocompetent cells such as Th17 cell, macrophage, neutrophil and the like, and has been clarified to play an important role in the aggravation of pathology in many autoimmune diseases such as rheumatoid arthritis, inflammatory bowel diseases (Crohn's disease, ulcerative colitis), multiple sclerosis, psoriasis and the like.

Recently, it has been reported that anti-IL-17 antibody preparations show a treatment effect on psoriasis patients (non-patent document 4). However, antibody preparations are very expensive, and problems are known that autoantibody to the antibody preparation is produced in the process of continuous use thereof, which impairs the effectiveness (secondary ineffective) and the like. Therefrom it is considered that a vaccine targeting IL-17 is effective for these diseases, and provides an effective therapeutic agent at a low cost for a long term.

As a vaccine against IL-17, study of peptide vaccine using full-length IL-17 as an immunogen has been reported (non-patent document 5). However, when the full-length IL-17 is used for immunization, cellular immunity to IL-17 is also induced, cytotoxic T cell attacks the cells expressing IL-17 and harmful side effects may strongly appear. In addition, an antibody showing cross-reactivity with other cytokine similar to IL-17 may also be produced. Therefore, a vaccine using only a partial epitope of IL-17 having no homology with other proteins as an immunogen is considered to be desirable from the aspect of safety. It has been reported that 2 kinds of IL-17 epitope vaccine were produced and administered to inflammatory bowel disease model mouse (non-patent document 6). In this report, however, pathology was not improved but aggravated in the vaccine administration group, and inflammation and collagen deposition in the large intestine increased.

As mentioned above, while there are reports on IL-17 epitope vaccines, the applicant is not aware of any report showing a treatment effect of the vaccine on some disease.

DOCUMENT LIST

Non-Patent Documents non-patent document 1: Nature Immunology, 2009, 10(7): 778-785
non-patent document 2: J Immunology, 2012, 188(8):3567-3571
non-patent document 3: Eur J Immunology 2012, 42(9): 2274-2284
non-patent document 4: J Dermatol 2014; 41: 1039-1046
non-patent document 5: Eur J Immunology 2006, 36(11): 2857-2867
non-patent document 6: Immunotherapy, 2012, 4(12):1799-1807

SUMMARY OF THE INVENTION

Problems to be Solved by the Invention

The present invention aims to provide a vaccine against IL-17A, an agent for the treatment and/or prophylaxis of a disease, in which IL-17A is involved in the aggravation of pathology such as SLE, and containing the vaccine, and the like.

Means of Solving the Problems

The present inventors have conducted intensive studies and specified, from the structure of IL-17A, an amino acid region important for binding to IL-17A receptor. Using a part of the amino acid region as an antigen, a polynucleotide encoding same was inserted into a vector encoding hepatitis B virus core antigen polypeptide to produce a DNA vaccine. The DNA vaccine was administered to NZBWF1 mouse as an SLE model mouse. As a result, a high increase in the antibody titer was observed, and production of an antibody correctly recognizing IL-17A was confirmed by a binding test of the antibody and the recombinant IL-17A. In addition, blood TNF-α decreased in MRL/lpr mouse as another SLE model mouse administered with the DNA vaccine, and blood IL-1β decreased in NZBWF1 mouse. Furthermore, by long-term observation of the DNA vaccine administration group in the NZBWF1 mice, significant elongation of the survival period was observed in the DNA vaccine administration group. Also, improved pathological findings in the kidney of NZBWF1 mouse, a decrease in F4/80 expression, and a decrease in the spleen weight of MRL/lpr mouse were observed, whereby improving effects of the DNA vaccine in SLE pathology could be confirmed.

In addition, the present inventors have confirmed that the pathology can be improved in colitis model mouse, arthritis model mouse, colon cancer-transplanted mouse, lung cancer-transplanted mouse, by the administration of the DNA vaccine or a peptide vaccine encoded by the DNA.

Surprisingly, the present inventors confirmed that aggravation of pathology, which is observed in conventionally-reported IL-17 epitope vaccines, is not found in the vaccine administration group in the present invention.

Based on these findings, the present inventors have completed the present invention.

That is, the present invention relates to the following.
[1] A vaccine for the prophylaxis or treatment of a disease involving IL-17A as an aggravation factor, comprising any of the following (1)-(3):
(1) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8,
(2) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8, wherein 1 or several amino acid residues are substituted, deleted, inserted or added, and
(3) an expression vector capable of expressing the polypeptide of the above-mentioned (1) or (2);
[2] the vaccine of [1], comprising any of the following (1)-(3):
(1) a polypeptide consisting of the amino acid sequence shown in SEQ ID NO: 1 or the amino acid sequence shown in SEQ ID NO: 8;
(2) a polypeptide consisting of the amino acid sequence shown in SEQ ID NO: 11 or the amino acid sequence shown in SEQ ID NO: 12; and
(3) an expression vector capable of expressing the polypeptide of the above-mentioned (1) or (2);
[3] the vaccine of [1] or [2], wherein the expression vector comprises a nucleotide sequence encoding hepatitis B virus core (HBc),
[4] the vaccine of [1] or [2], wherein the expression vector comprises a nucleotide sequence wherein the nucleotide sequence encoding the polypeptide of (1) or (2) is inserted between nucleotide No:246 and nucleotide No:247 of the nucleotide sequence shown in SEQ ID NO: 17,
[5] the vaccine of [1]-[4], comprising a carrier protein and/or an adjuvant,
[5-1] a composition comprising the vaccine of any of [1]-[5],
[6] the vaccine of [1]-[5], wherein the disease involving IL-17A as an aggravation factor is selected from the group consisting of SLE, inflammatory bowel disease, rheumatoid arthritis, tumor, psoriasis and multiple sclerosis,
[7] the vaccine of [1]-[6] comprising the following (1) or (2), wherein the disease involving IL-17A as an aggravation factor is selected from the group consisting of SLE, inflammatory bowel disease, rheumatoid arthritis, colon cancer, and lung cancer:
(1) a polypeptide consisting of the amino acid sequence shown in SEQ ID NO: 1, and
(2) an expression vector capable of expressing the polypeptide of the above-mentioned (1),
[8] the vaccine of [1]-[6] comprising any of the following (1)-(3), wherein the disease involving IL-17A as an aggravation factor is rheumatoid arthritis:
(1) a polypeptide consisting of the amino acid sequence shown in SEQ ID NO: 1;
(2) a polypeptide consisting of the amino acid sequence shown in SEQ ID NO: 11 or the amino acid sequence shown in SEQ ID NO: 12; and
(3) an expression vector capable of expressing the polypeptide of the above-mentioned (1) or (2);
[9] a prophylactic or therapeutic agent for a disease involving IL-17A as an aggravation factor, comprising an antibody that recognizes the polypeptide of the following (1) or (2) and inhibits the function of IL-17A:
(1) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8,
(2) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8, wherein 1 or several amino acid residues are substituted, deleted, inserted or added,
[10] the prophylactic or therapeutic agent of [9], comprising an antibody that recognizes the polypeptide of the following (1) or (2) and inhibits the function of IL-17A:
(1) a polypeptide consisting of the amino acid sequence shown in SEQ ID NO: 1 or the amino acid sequence shown in SEQ ID NO: 8;
(2) a polypeptide consisting of the amino acid sequence shown in SEQ ID NO: 11 or the amino acid sequence shown in SEQ ID NO: 12,
[10-1] the prophylactic or therapeutic agent of [9] or [10], wherein the disease involving IL-17A as an aggravation factor is selected from the group consisting of SLE, inflammatory bowel disease, psoriasis, rheumatoid arthritis, multiple sclerosis, encephalomyelitis, tumor (various neoplastic diseases involving IL-17A as an aggravation factor, including non-small cell lung cancer, colon cancer, blood cell tumor and the like), arteriosclerosis, chronic inflammatory diseases, and allergic disease (delayed-type hypersensitivity, contact-type hypersensitivity),

[11] the prophylactic or therapeutic agent of [9] or [10], wherein the disease involving IL-17A as an aggravation factor is selected from the group consisting of SLE, inflammatory bowel disease, rheumatoid arthritis, tumor, psoriasis and multiple sclerosis,

[11-1] the prophylactic or therapeutic agent of [9] or [10], wherein the disease involving IL-17A as an aggravation factor is SLE,

[12] the prophylactic or therapeutic agent of [9]-[11], comprising an antibody that recognizes a polypeptide consisting of the amino acid sequence shown in SEQ ID NO: 1 and inhibits the function of IL-17A, wherein the disease involving IL-17A as an aggravation factor is selected from the group consisting of SLE, inflammatory bowel disease, rheumatoid arthritis, colon cancer, and lung cancer,

[13] the prophylactic or therapeutic agent of [9]-[11], comprising a polypeptide consisting of the amino acid sequence shown in SEQ ID NO: 1, the amino acid sequence shown in SEQ ID NO: 11 or the amino acid sequence shown in SEQ ID NO: 12, wherein the disease involving IL-17A as an aggravation factor is rheumatoid arthritis,

[14] a polypeptide consisting of the amino acid sequence shown in SEQ ID NO: 1,

[14-1] a polypeptide encoding [14].

Effect of the Invention

The vaccine of the present invention can be used for the treatment and the like of diseases involving IL-17A as an aggravation factor of pathology such as SLE.

Figure 18:
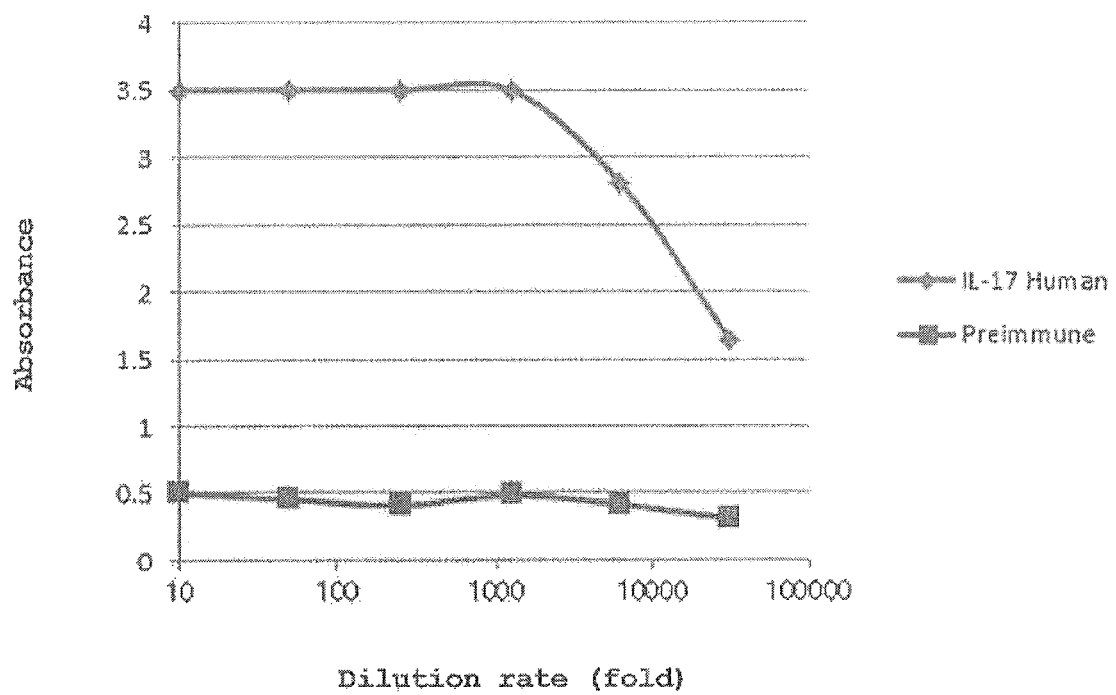

FIG. 18 shows binding of an antiserum (IL-17 Human) obtained from a mouse immunized with a vaccine containing a peptide consisting of human IL-17A1 epitope (SEQ ID NO: 1) or serum before vaccine administration (Preimmune) and BSA-human IL-17A1 conjugate. The primary antibody (mouse antiserum) was diluted 10-fold, and then serially diluted by 5-fold and used.

Figure 19:
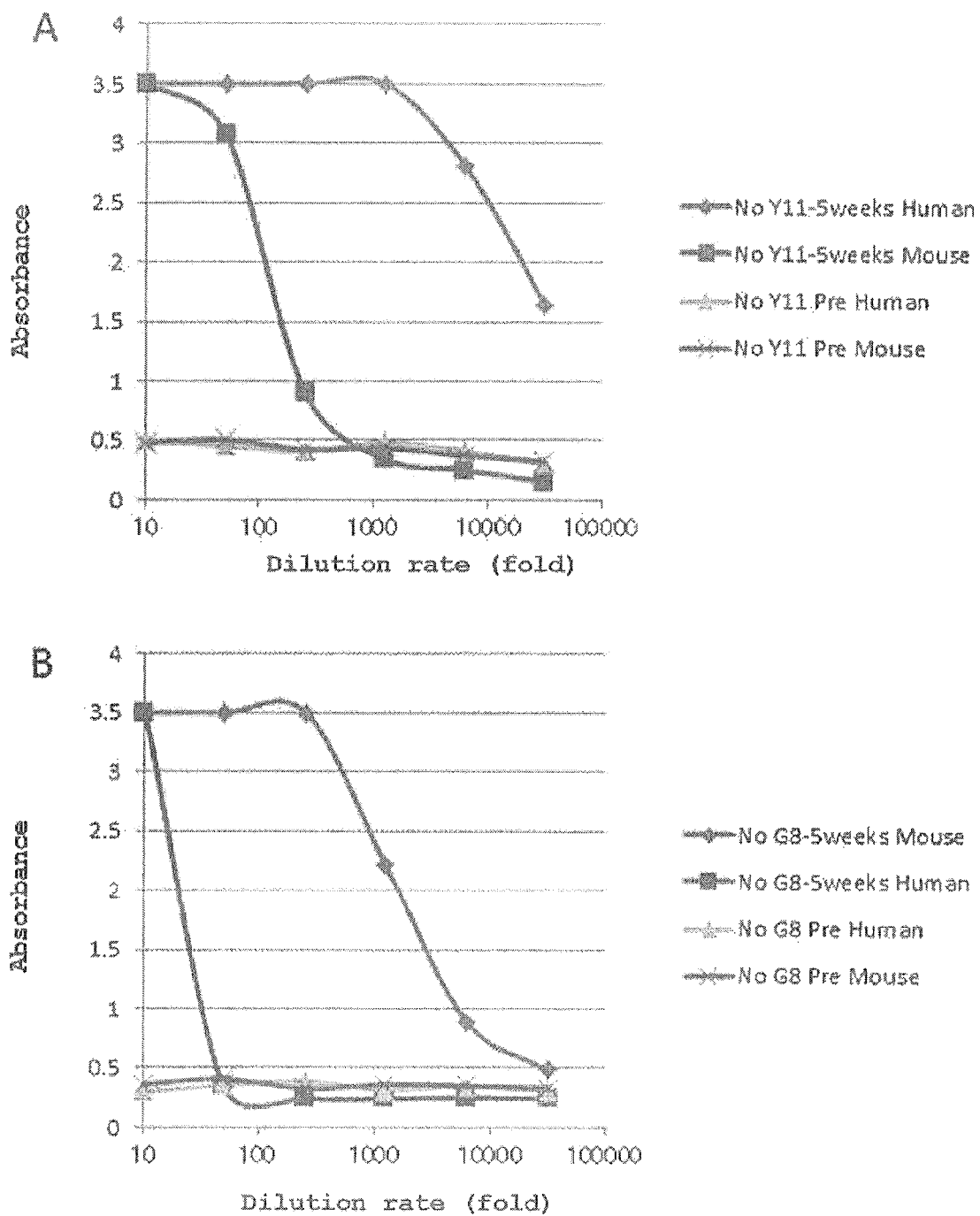

FIG. 19 shows A) binding of an antiserum obtained from a mouse immunized with a vaccine containing a peptide consisting of human IL-17A1 epitope (SEQ ID NO: 1) and BSA-human IL-17A1 conjugate (No Y11-5 weeks Human), or BSA-mouse IL-17A1 conjugate (No Y11-5 weeks Mouse). It also shows binding of serum before vaccine administration and BSA-human IL-17A1 conjugate (No Y11 Pre Human), or BSA-mouse IL-17A1 conjugate (No Y11 Pre Mouse). The primary antibody (mouse antiserum) was diluted 10-fold, and then serially diluted by 5-fold and used. B) shows binding of an antiserum obtained from a mouse immunized with a vaccine containing a peptide consisting of mouse IL-17A1 epitope (SEQ ID NO: 5) and BSA-mouse IL-17A1 conjugate (No G8-5 weeks Mouse), or BSA-human IL-17A1 conjugate (No G8-5 weeks Human). It also shows binding of serum before vaccine administration and BSA-mouse IL-17A1 conjugate (No G8 Pre Mouse), or BSA-human IL-17A1 conjugate (No G8 Pre Human). The primary antibody (mouse antiserum) was diluted 10-fold, and then serially diluted by 5-fold and used.

Figure 20:
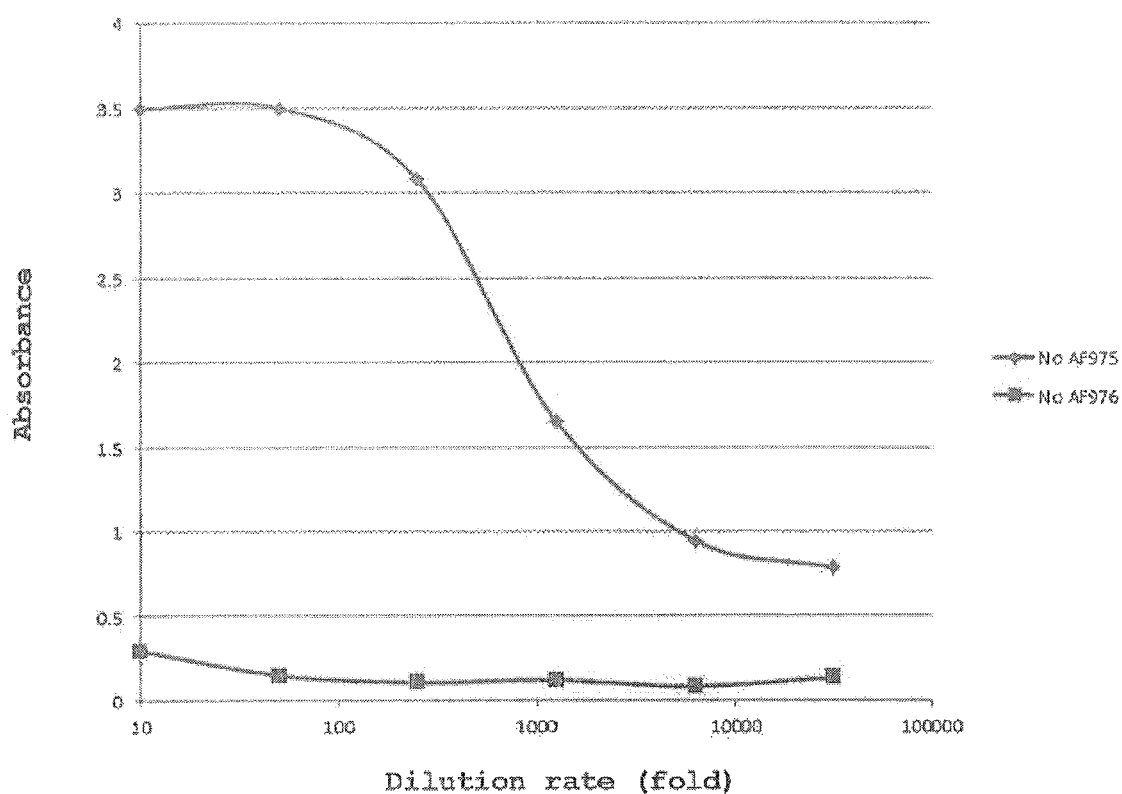

FIG. 20 shows binding of an antiserum obtained from a mouse immunized with a vaccine containing a peptide consisting of human IL-17A2 epitope (SEQ ID NO: 8) and BSA-human IL-17A2 conjugate (No AF975), or binding of an antiserum obtained from a mouse immunized with a vaccine containing a peptide consisting of human IL-17A3 epitope (SEQ ID NO: 9) and BSA-human IL-17A3 conjugate (No AF976). The primary antibody (mouse antiserum) was diluted 10-fold, and then serially diluted by 5-fold and used.

Figure 21:
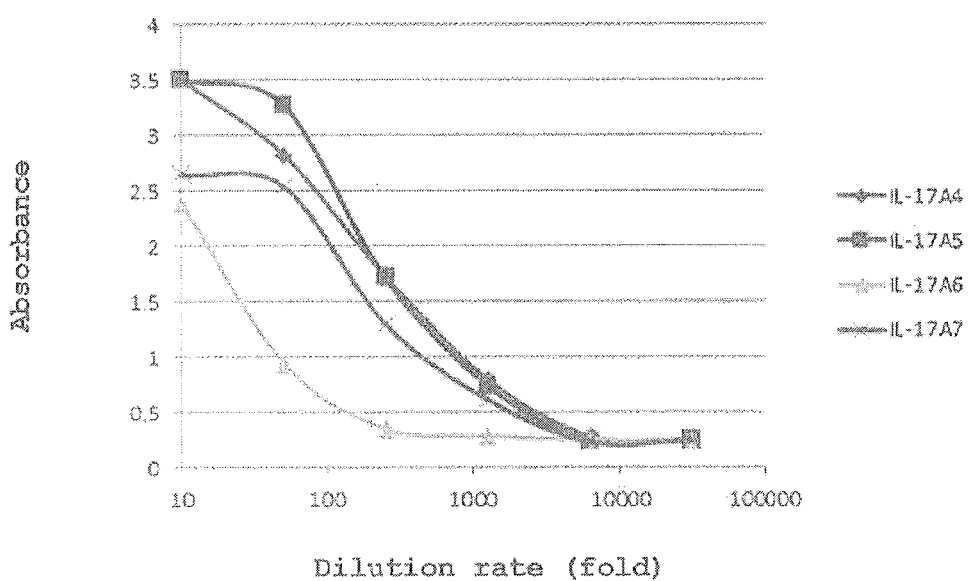

FIG. 21 shows an increase in the antibody titer on week 6 of BALB/c mouse immunized with a vaccine containing a peptide consisting of human IL-17A4 epitope (SEQ ID NO: 11), a vaccine containing a DNA encoding human IL-17A5 epitope (SEQ ID NO: 12), a vaccine containing a DNA encoding human IL-17A6 epitope (SDY), or a vaccine containing a DNA encoding human IL-17A7 epitope (DYY). Each primary antibody (mouse antiserum) was diluted 10-fold, and then serially diluted by 5-fold and used.

Figure 22:
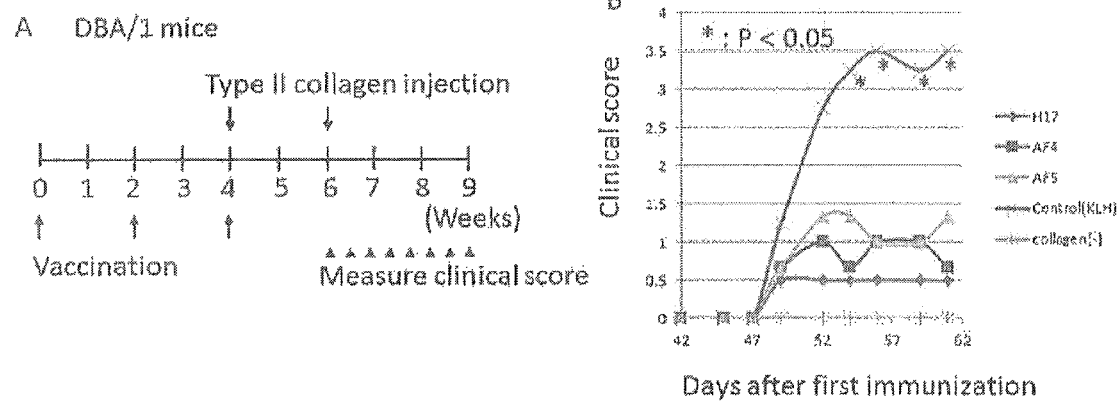

FIG. 22 shows A) a plan of administration of various IL-17A peptide vaccines and Type II collagen to DBA/1 mouse. B) shows the clinical score of arthritis of DBA/1 mouse administered with various IL-17A peptide vaccines and Type II collagen. H17: human IL-17A1 epitope, AF4: human IL-17A4 epitope, AF5: human IL-17A2 epitope, Control (KLH): KLH, Collagen(–): Type II collagen non-administration.

Figure 23:
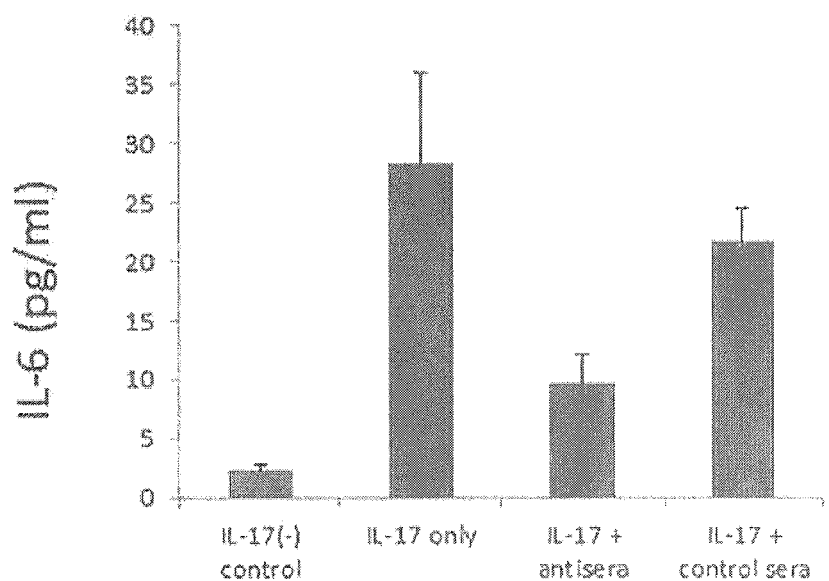

FIG. 23 shows measurement results of the concentration of IL-6 secreted by normal human dermal fibroblast (NHDF) in a medium by ELISA. IL-17(–) control: IL-17 no addition, IL-17 only: recombinant human IL-17A addition, IL-17+ antisera: recombinant human IL-17A and anti-human IL-17A1 mouse antibody, IL-17+antisera: recombinant human IL-17A and non-immune mouse antibody

DESCRIPTION OF EMBODIMENTS

The present invention provide a vaccine to IL-17A, an agent containing the vaccine for the treatment and/or pro-phylaxis of diseases involving IL-17A as an aggravation factor of pathology such as SLE, and the like.

Vaccine

The vaccine of the present invention to IL-17A (also referred to as epitope vaccine) is selected from the group consisting of the following (1)-(3).

(1) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8, (2) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8, wherein 1 or several amino acid residues are substituted, deleted, inserted or added, and (3) an expression vector capable of expressing the polypeptide of the above-mentioned (1) or (2).

Of these, the vaccine of the present invention to IL-17A is preferably selected from the group consisting of the following (1')-(3').

(1') a polypeptide consisting of the amino acid sequence shown in SEQ ID NO: 1 or the amino acid sequence shown in SEQ ID NO: 8, (2') a polypeptide consisting of the amino acid sequence shown in SEQ ID NO: 11 or the amino acid sequence shown in SEQ ID NO: 12, and (3') an expression vector capable of expressing the polypeptide of the above-mentioned (1') or (2').

Most preferably, the vaccine of the present invention to IL-17A is preferably selected from the group consisting of the following (1") and (2").

(1") a polypeptide consisting of the amino acid sequence shown in SEQ ID NO: 1, the amino acid sequence shown in SEQ ID NO: 11 or the amino acid sequence shown in SEQ ID NO: 12, and (2") an expression vector capable of expressing the polypeptide of the above-mentioned (1").

The disease involving IL-17A as an aggravation factor is not particularly limited as long as the pathology is aggravated by IL-17A. For example, SLE, inflammatory bowel diseases (ulcerative colitis, Crohn's disease), psoriasis, rheumatoid arthritis, multiple sclerosis, encephalomyelitis, tumors (lung cancer (particularly, non-small cell lung cancer is suitable), various neoplastic diseases involving IL-17A in the aggravation, including colon cancer, blood cell tumor and the like), arteriosclerosis, chronic inflammatory diseases, and allergic diseases (delayed-type hypersensitivity, contact-type hypersensitivity etc.) and the like can be mentioned. Suitable disease includes SLE, inflammatory bowel disease, rheumatoid arthritis, lung cancer, colon cancer, psoriasis, and multiple sclerosis, and most suitable disease includes SLE, inflammatory bowel disease, rheumatoid arthritis, lung cancer, and colon cancer. As described in the below-mentioned Examples, a polypeptide consisting of the amino acid sequence shown in SEQ ID NO: 1 and DNA encoding the polypeptide showed a treatment effect on SLE, inflammatory bowel disease, rheumatoid arthritis, lung cancer and colon cancer. In addition to a polypeptide consisting of the amino acid sequence shown in SEQ ID NO: 1, polypeptides consisting of the amino acid sequence shown in SEQ ID NO: 11, the amino acid sequence shown in SEQ ID NO: 12 and DNA encoding the polypeptide also showed a treatment effect on rheumatoid arthritis. Aggravation refers to further exacerbation of pathology and the level of exacerbation is not questioned.

The subject of administration of the vaccine of the present invention may be any mammal, which is a mammal who has developed a disease involving IL-17A in the aggravation of pathology or having a risk of developing the disease. Examples of the mammal include experiment animals such as rodents (e.g., mouse, rat, hamster, guinea pig and the like), rabbit and the like, pets such as dog, cat and the like, domestic animals such as bovine, swine, goat, horse, sheep and the like, primates such as human, monkey, orangutan, chimpanzee and the like, and the like, and human is preferable. The subject of administration may or may not be undergoing treatments.

When the vaccine of the present invention is administered, substances contained in the vaccine are preferably those derived from the subject of administration (that is, when administered to human, the vaccine is a substance derived from human, and when administered to mouse, the vaccine is a substance derived from mouse).

The polypeptide of the above-mentioned (1) (or (1'), (1")), hereinafter the same) (hereinafter also the polypeptide of the present invention, including the polypeptide of the above-mentioned (2) (or (2'), (2"), hereinafter the same)) contained in the vaccine of the present invention is a partial amino acid sequence of IL-17A.

In the present invention, the sequence of the 62nd-69th amino acids of human IL-17A is SEQ ID NO: 1, and the sequence of the 65th-72nd amino acids of the corresponding mouse IL-17A is SEQ ID NO: 5. These are encoded by, for example, the nucleotide sequences shown in SEQ ID NO: 2 and SEQ ID NO: 6, respectively. In addition, the sequence of the 102nd-118th amino acids of human IL-17A is SEQ ID NO: 8, and the sequence of the 105th-121st amino acids of the corresponding mouse IL-17A is SEQ ID NO: 10. These are encoded by, for example, the nucleotide sequences shown in SEQ ID NO: 13 and SEQ ID NO: 14, respectively.

An amino acid sequence derived from a non-human mammal, which corresponds to SEQ ID NO: 1 (SEQ ID NO: 8), can be obtained easily by designing appropriate primers and probes by utilizing the information of the sequence disclosed in SEQ ID NO: 1 (SEQ ID NO: 8) in the present specification, known sequence database and the like, and using a general genetic engineering method such as RT-PCR, plaque hybridization and the like.

The polypeptide of the above-mentioned (2) to be contained in the vaccine of the present invention is a partial sequence of the amino acid sequence of IL-17A wherein 1 or several (preferably 1-several (2-5)) amino acids are deleted, substituted, inserted or added. Such polypeptide includes, in the case of human, the amino acid sequence shown in SEQ ID NO: 1 (SEQ ID NO: 8) wherein 1 or several (preferably 1-several (2-5)) amino acids are deleted, substituted, inserted or added. Examples of the amino acid sequence include (1) the amino acid sequence shown in SEQ ID NO: 1 (SEQ ID NO: 8) wherein 1 or several (preferably 1-several (2-5)) amino acids are deleted, (2) the amino acid sequence shown in SEQ ID NO: 1 (SEQ ID NO: 8) added with 1 or several (preferably 1-several (2-5)) amino acids, (3) the amino acid sequence shown in SEQ ID NO: 1 (SEQ ID NO: 8) inserted with 1 or several (preferably 1-several (2-5)) amino acids, (4) the amino acid sequence shown in SEQ ID NO: 1 (SEQ ID NO: 8) wherein 1 or several (preferably 1-several (2-5)) amino acids are substituted by other amino acids, and (5) an amino acid sequence having the above-mentioned mutations (1)-(4) in combination (in this case, the total of the mutated amino acids is 1 or several (preferably 1-several (2-5))).

In addition, as the amino acid sequence to be contained in the polypeptide of above-mentioned (2), an amino acid sequence derived from a non-human mammal, which corresponds to SEQ ID NO: 1 (SEQ ID NO: 8) and in which 1 or several (preferably 1-several (2-5)) amino acids are deleted, substituted, inserted or added can be preferably mentioned.

Such polypeptide includes, in the case of mouse, the amino acid sequence shown in SEQ ID NO: 5 (SEQ ID NO: 10) wherein 1 or several (preferably 1-several (2-5)) amino acids are deleted, substituted, inserted or added. Examples of the amino acid sequence include (1) the amino acid sequence shown in SEQ ID NO: 5 (SEQ ID NO: 10) wherein 1 or several (preferably 1-several (2-5)) amino acids are deleted, (2) the amino acid sequence shown in SEQ ID NO: 5 (SEQ ID NO: 10) added with 1 or several (preferably 1-several (2-5)) amino acids, (3) the amino acid sequence shown in SEQ ID NO: 5 (SEQ ID NO: 10) inserted with 1 or several (preferably 1-several (2-5)) amino acids, (4) the amino acid sequence shown in SEQ ID NO: 5 (SEQ ID NO: 10) wherein 1 or several (preferably 1-several (2-5)) amino acids are substituted by other amino acids, and (5) an amino acid sequence having the above-mentioned mutations (1)-(4) in combination (in this case, the total of the mutated amino acids is 1 or several (preferably 1-several (2-5))).

Examples of the "substitution of amino acid residue" include preservative amino acid substitution. The preservative amino acid substitution refers to substitution of a particular amino acid with an amino acid having a side chain having properties similar to those of the side chain of the amino acid. Specifically, in the preservative amino acid substitution, a particular amino acid is substituted by other amino acid in the group to which the amino acid belongs. The group of amino acids having a side chain with similar properties is known in the pertinent field. Examples of the group of such amino acids include amino acids having a basic side chain (e.g., lysine, arginine, histidine), amino acids having an acidic side chain (e.g., aspartic acid, glutamic acid), amino acids having a neutral side chain (e.g., glycine, asparagine, glutamine, serine, threonine, tyrosine, cysteine, alanine, valine, leucine, isoleucine, proline, phenylalanine, methionine, tryptophan). The amino acids having a neutral side chain can be further divided into amino acid having a polar side chain (e.g., glycine, asparagine, glutamine, serine, threonine, tyrosine, cysteine), and amino acid having a nonpolar side chain (e.g., alanine, valine, leucine, isoleucine, proline, phenylalanine, methionine, tryptophan). As other group, for example, amino acids having an aromatic side chain (e.g., phenylalanine, tryptophan, tyrosine), amino acids having a side chain containing a hydroxyl group (alcoholic hydroxyl group, phenolic hydroxyl group) (e.g., serine, threonine, tyrosine) and the like can also be mentioned.

Examples of the "deletion of amino acid residue" include selection and deletion of any amino acid residue of the amino acid sequence shown in SEQ ID NO: 1. Examples of such amino acid sequence include SEQ ID NO: 11, SEQ ID NO: 12, SDY and DYY. Preferred are SEQ ID NO: 11 and SEQ ID NO: 12. These are encoded by, for example, the nucleotide sequences shown in SEQ ID NO: 15 and SEQ ID NO: 16, respectively.

Examples of the "insertion of amino acid residue" or "addition of amino acid residue" include insertion or addition of amino acid residue inside or to the N-terminus side or C-terminus side of the amino acid sequence shown in SEQ ID NO: 1. To enhance water solubility of peptide, 1 or 2 residues of arginine (Arg) or lysine (Lys), which are basic amino acids, may be added to the N-terminus side or C-terminus side of the amino acid sequence.

The polypeptide of the present invention may contain additional amino acids. Addition of such amino acids is acceptable as long as the polypeptide induces a specific immune reaction to IL-17A. While the amino acid sequence to be added is not particularly limited, for example, a tag that facilitates detection, purification and the like of the polypeptide can be mentioned. Examples of the tag include Flag tag, histidine tag, c-Myc tag, HA tag, AU1 tag, GST tag, MBP tag, fluorescence protein tag (e.g., GFP, YFP, RFP, CFP, BFP etc.), immunoglobulin Fc tag and the like. The position at which the amino acid sequence is added is N-terminus and/or C-terminus of the polypeptide of the present invention.

While the amino acid to be used for the polypeptide of the present invention encompasses an L form, D form and DL form, it is generally preferably an L form. These polypeptides can be synthesized by a general polypeptide synthesis method and subjected to the present invention. In the present invention, the production method, synthesis method, supply method and the like are not particularly limited.

In the expression vector of the above-mentioned (3) (or (3'), (2''), hereinafter the same), a polynucleotide encoding the polypeptide of the aforementioned (1) or (2) (DNA or RNA, preferably DNA) is functionally linked to the downstream of a promoter capable of exhibiting the promoter activity in the cells of a mammal to be the subject of administration. That is, the expression vector of (3) can express the polypeptide of (1) or (2) as a transcription product under the control of the promoter. By the administration of the expression vector of (3) to a mammal, the polypeptide of (1) or (2) is produced in the body of the mammal, whereby a specific immune reaction to the polypeptide of (1) or (2) is induced in the mammal.

The promoter to be used may be any as long as it can function in the cells of a mammal to be the subject of administration, and polI type promoter, polII type promoter, polIII type promoter and the like can be used. Specifically, initial promoter derived from SV40, virus promoters such as cytomegalovirus (CMV) and the like, constituent protein gene promoter of a mammal such as β-actin gene promoter and the like, and the like are used.

A transcription termination signal, i.e., terminator region, is preferably contained at the downstream of the polynucleotide encoding the polypeptide of the aforementioned (1) or (2). Furthermore, it may further contain a selection marker gene (gene imparting resistant to drugs such as tetracycline, ampicillin, kanamycin and the like, gene complementing auxotrophic mutation etc.) for the selection of a transformed cell.

While the kind of the vector to be used as an expression vector in the present invention is not particularly limited, a vector preferable for the administration to a mammal such as human and the like includes virus vector, plasmid vector and the like. Examples of the virus vector include retrovirus, adenovirus, adeno-associated virus and the like. In consideration of the production, easy handleability and economic efficiency, a plasmid vector is preferably used. Particularly preferred is an expression vector containing a polynucleotide encoding hepatitis B virus core (hereinafter to be referred to as HBc), for which WO 2012/141280 and the like can be referred to.

HBc has the property to become spherical by self-assembly, and IL-17A epitope can be presented stably while maintaining the structure thereof on the outside of the core particles formed by self-assembly. HBc and IL-17A epitope may be directly linked by a covalent bond or may be linked via a spacer. The spacer may be any as long as IL-17A epitope is presented stably while maintaining the structure thereof on the outside of the core particles formed by self-assembly of HBc. Examples thereof include, but are not limited to, IT, GAT, CGG and the like. Examples of the plasmid vector containing the sequence include, but are not limited to, pCAGGS, pCR-X8, pcDNA3.1, pZeoSV, pBK-CMV and the like. More preferred is pcDNA3.1-HBc vector. In this vector, a spacer is inserted between the 240th and 241st bases of a polynucleotide encoding HBc, which correspond to the 80th and 81st amino acids of HBc. Therefore, the expression vector of the above-mentioned (3) is preferably an expression vector containing a nucleotide sequence wherein a nucleotide sequence encoding the polypeptide of the aforementioned (1) or (2) is inserted between base No.:246 and base No.:247 of the nucleotide sequence shown in SEQ ID NO: 17.

The vaccine of the present invention can be provided as a pharmaceutical composition containing any carrier, for example, a pharmaceutically acceptable carrier, in addition to the polypeptide of the above-mentioned (1) or (2) or the expression vector of (3).

Examples of the pharmaceutically acceptable carrier include, but are not limited to, excipients such as sucrose, starch and the like, binders such as cellulose, methylcellulose and the like, disintegrants such as starch, carboxymethylcellulose and the like, lubricants such as magnesium stearate, aerogel and the like, aromatics such as citric acid, menthol and the like, preservatives such as sodium benzoate, sodium bisulfite and the like, stabilizers such as citric acid, sodium citrate and the like, suspending agents such as methylcellulose, polyvinylpyrrolidone and the like, dispersing agents such as surfactant and the like, diluents such as water, saline and the like, base-wax and the like.

When the vaccine of the present invention is the expression vector of the above-mentioned (3), to promote introduction of the expression vector into the cell, the vaccine of the present invention can further contain a reagent for the introduction of the nucleic acid. When a virus vector is used as the expression vector, RetroNectin, fibronectin, polybrene and the like can be used as the transgene reagent. When a plasmid vector is used as an expression vector, cationic lipids such as Lipofectin, lipofectamine, DOGS (Transfectam), DOPE, DOTAP, DDAB, DHDEAB, HDEAB, polybrene, or poly(ethyleneimine) (PEI) and the like can be used.

The vaccine of the present invention may further contain a carrier protein to increase the immunogenicity of the polypeptide of the above-mentioned (1) or (2) or the polypeptide encoded by the expression vector of (3). A carrier protein is generally a substance that binds to a molecule having no immunogenicity due to its small molecular weight and imparts the immunogenicity, and is known in the Technical Field. Examples of the carrier protein include bovine serum albumin (BSA), rabbit serum albumin (RSA), ovalbumin (OVA), keyhole-limpet hemocyanin (KLH), thyroglobulin (TG), immunoglobulin and the like. In the case of the above-mentioned expression vector of (3), a polynucleotide encoding the carrier protein may be linked to a polynucleotide encoding the polypeptide of the above-mentioned (1) or (2).

Also, the vaccine of the present invention may further contain a pharmaceutically acceptable adjuvant compatible with the active ingredient. Adjuvant is generally a substance that non-specifically potentiates an immune response of the host, and a number of various adjuvants are known in the technical field. Examples of the adjuvant include, but are not limited to, the following: complete Freund's adjuvant, incomplete Freund's adjuvant, aluminum hydroxide, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycerol-3-hydroxyphosphoryloxy)-ethylamine (MTP-PE), Quill A (registered trade mark), lysolecithin, saponin derivative, pluronic polyol, montanide ISA-50 (Seppic, Paris, France), Bayol (registered trade mark) and Markol (registered trade mark).

The vaccine of the present invention can be administered orally or parenterally to a mammal. Since polypeptide and expression vector are decomposed in the stomach, parenteral administration is preferable. A preparation preferable for oral administration includes liquid, capsule, sachet, tablet, suspension, emulsion and the like. A preparation preferable for parenteral administration (e.g., subcutaneous injection, muscular injection, topical injection, intraperitoneal administration and the like) includes aqueous and non-aqueous isotonic, aseptic injection liquid, which optionally contains antioxidant, buffer, bacteriostatic agent, isotonicity agent and the like. Also, an aqueous and non-aqueous aseptic suspending agent can be mentioned, and the agent optionally contains suspending agent, solubilizer, thickener, stabilizer, preservative and the like. Such preparation can be sealed in a unit dose or plural dose container such as ampoule or vial. In addition, the active ingredient and pharmaceutically acceptable carriers may be freeze-dried, and preserved in a form only requiring dissolution or suspending in a suitable aseptic vehicle immediately before use.

The content of the active ingredient in a pharmaceutical composition is generally about 0.1-100 wt %, preferably about 1-99 wt %, more preferably about 10-90 wt %, of the whole pharmaceutical composition.

While the dose of the vaccine of the present invention varies depending on the administration subject, administration method, administration form and the like, when the active ingredient is the polypeptide of the above-mentioned (1) or (2), 1 µg-1000 µg, preferably 20 µg-100 µg, of the polypeptide is generally administered per dose to an adult 2 or 3 times for generally 4 weeks to 12 weeks. When the antibody titer falls, addition administration is performed once each time. When the active ingredient is the expression vector of the above-mentioned (3), 1 µg-1000 µg, preferably 20 µg-100 µg, of the polypeptide is generally administered per dose to an adult 2 or 3 times for generally 4 weeks to 12 weeks. When the antibody titer falls, addition administration is performed once each time.

By the administration of the vaccine of the present invention to a mammal, immune responses specific to IL-17A (specific antibody production, growth of specific T cells etc.) are induced, the mammal acquires a neutralizing antibody to IL-17A, and the function of IL-17A is inhibited, whereby a prophylactic or therapeutic effect is provided on a disease involving IL-17A as an aggravation factor.

In addition, the present invention provides a kit composed of one or more containers containing one or more components of the vaccine of the present invention. A disease involving IL-17A as an aggravation factor can also be prevented, or the symptoms thereof can also be treated or alleviated using the kit of the present invention.

IL-17A Neutralizing Antibody for Prophylaxis or Treatment of Disease Involving IL-17A as Aggravation Factor The present invention provides a prophylactic or therapeutic agent for a disease involving IL-17A as an aggravation factor, which contains an antibody that recognizes the polypeptide of the following (1) or (2) and inhibits the function of IL-17A (the prophylactic or therapeutic agent of the present invention).

(1) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8, and (2) a polypeptide comprising the amino acid sequence shown in SEQ ID NO: 1, the amino acid sequence shown in SEQ ID NO: 8, an amino acid sequence derived from a non-human mammal, which corresponds to SEQ ID NO: 1, or an amino acid sequence derived from a non-human mammal, which corresponds to SEQ ID NO: 8, wherein 1 or several amino acid residues are substituted, deleted, inserted or added.

In addition, the prophylactic or therapeutic agent of the present invention preferably contains an antibody that recognizes the polypeptide of the following (1') or (2') and inhibits the function of IL-17A.

(1') a polypeptide consisting of the amino acid sequence shown in SEQ ID NO: 1 or the amino acid sequence shown in SEQ ID NO: 8; and (2') a polypeptide consisting of the amino acid sequence shown in SEQ ID NO: 11 or the amino acid sequence shown in SEQ ID NO: 12.

Most preferably, the prophylactic or therapeutic agent of the present invention contains (1") an antibody that recognizes the polypeptide consisting of the amino acid sequence shown in SEQ ID NO: 1 and inhibits the function of IL-17A.

An antibody that recognizes the aforementioned polypeptide of (1) or (2) (or (1'), (2') or (1"), hereinafter the same) binds to IL-17A and inhibits the function thereof, and therefore, can be an effective prophylactic and/or therapeutic means for the aforementioned disease involving IL-17A as an aggravation factor. That is, administration of the antibody is expected to show a therapeutic effect for patients who have developed a disease involving IL-17A as an aggravation factor, and a prophylactic effect for subjects having a risk of developing a disease involving IL-17A as an aggravation factor.

Of the aforementioned diseases involving IL-17A as an aggravation factor, the IL-17A neutralizing antibody of the present invention can be used for the prophylaxis and/or treatment of SLE, inflammatory bowel disease, rheumatoid arthritis, lung cancer, colon cancer, psoriasis and multiple sclerosis, particularly, SLE, inflammatory bowel disease, rheumatoid arthritis, lung cancer and colon cancer.

The antibody of the present invention includes natural antibodies such as polyclonal antibody, monoclonal antibody and the like, chimeric antibody that can be produced using transgenic mouse and gene recombination technique, humanized antibody and single strand antibody, human antibody produced by mouse, phage display and the like introduced with a human antibody-producing gene, fragments of these and the like. The antibody of the present invention is not particularly limited as long as it recognizes each polypeptide of the present invention, and inhibits the function of IL-17A. From the aspects of specificity to IL-17A, a monoclonal antibody is preferable. From the aspects of clinical application to human, the antibody of the present invention is preferably a humanized antibody or human antibody.

The above-mentioned antibody fragment means a region of one part of the aforementioned antibody, and specific examples thereof include F(ab')$_2$, Fab', Fab, antibody fragments including Fc regions, Fv (variable fragment of antibody), sFv, dsFv (disulphide stabilized Fv), dAb (single domain antibody) and the like (Exp. Opin. Ther. Patents, Vol. 6, No. 5, p. 441-456, 1996).

The above-mentioned humanized antibody refers to an antibody produced by the gene recombination technique to have an antigen recognition site derived from a gene other than human and the rest derived from a human gene. The above-mentioned human antibody refers to a human antibody produced by a transgenic mouse introduced with a human antibody producing gene (e.g., TransChromo Mouse (trade mark)), or an antibody produced based on a human antibody library in which an antibody variable region is expressed by the display technique such as phage display method and the like from a library constructed by randomly combining human B lymphocyte mRNA, and VH gene and VL gene derived from genome.

The class of the antibody is not particularly limited, and the antibody of the present invention encompasses antibodies having any isotype of IgG, IgM, IgA, IgD, IgE and the like. Preferred is IgG or IgM and, in consideration of the easiness of the purification of antibody and the like, more preferred is IgG.

Production Method of Antibody

Polyclonal antibody and monoclonal antibody can be produced by a method known per se. That is, in the case of a polyclonal antibody, a mammal, for example, mouse, rat, hamster, guinea pig, rabbit, cat, dog, swine, goat, horse, bovine and the like, preferably mouse, rat, hamster, guinea pig, goat, horse or rabbit, is immunized with an immunogen (the polypeptide of the present invention) together with Freund's adjuvant as necessary. In the case of a monoclonal antibody, mouse, rat, hamster and the like are immunized by a similar method.

While the polypeptide of the present invention can be directly used as an immunogen, it may be used for immunization as a complex with a polymer compound having a molecular weight of not less than 10,000 (e.g., carrier protein and the like). For example, a polypeptide consisting of the amino acid sequence shown in SEQ ID NO: 1 is synthesized according to the method described above, and a complex with a carrier protein such as bovine serum albumin (BSA), rabbit serum albumin (RSA), ovalbumin (OVA), keyhole-limpet hemocyanin (KLH), thyroglobulin (TG), immunoglobulin and the like is formed and may be used as an immunogen.

To form a complex of the aforementioned polypeptide and a carrier protein and the like, 1-2, preferably one amino acid can be added to the polypeptide of the present invention. While the position of amino acid to be added may be any position in the polypeptide and is not particularly limited, the N-terminus or C-terminus of the polypeptide is preferable.

In the formation of a complex, a method known per se can be applied as long as the antigenicity of the polypeptide of the present invention can be maintained. For example, a cysteine residue is introduced into the polypeptide of the present invention, and the polypeptide can be bound to the amino group of the aforementioned polymer compound (carrier protein) via an SH group which is the side chain of cysteine (MBS method). In addition, amino groups such as ε amino group, α amino group and the like of the lysine residue of a protein can also be bound to each other (glutaraldehyde method).

Polyclonal antibody can be specifically produced as follows. That is, mouse, rat, hamster, guinea pig, goat, horse or rabbit, preferably goat, horse or rabbit, more preferably rabbit, is immunized by subcutaneous, intramuscular, intravenous, intrafootpad or intraperitoneal injection of an immunogen 1-several times. Generally, immunization is performed 1-5 times every about 1-14 days from the initial immunization, and the serum is obtained from the immunized mammal about 1-5 days from the final immunization.

While serum per se can also be used as a polyclonal antibody, it is also possible to isolate and/or purify the antibody by ultrafiltration, ammonium sulfate fraction, euglobulin precipitation, caproinic acid method, caprylic acid method, ion exchange chromatography (DEAE or DE52 etc.), affinity column chromatography using an anti-immunoglobulin column or protein A/G column, a column crosslinked with immunogen and the like and use the obtained purified antibody.

Examples of the production method of the monoclonal antibody include the following methods. A hybridoma is prepared from antibody-producing cells obtained from the above-mentioned immunized animal and myeloma cells without an autoantibody producing ability, and the hybridoma is cloned. That is, a clone that produces a monoclonal antibody showing specific affinity for the peptide of the present invention used for immunizing the mammal and does not show intersection reactivity with a carrier protein is selected using the culture supernatant of hybridoma as a sample and by an immunological method. Then, an antibody can be produced from the culture supernatant and the like of the hybridoma by a method known per se.

To be specific, a monoclonal antibody can be produced as follows. That is, mouse, rat or hamster (including transgenic animal generated to produce an antibody derived from other animal such as human antibody producing transgenic mouse) is immunized by subcutaneous, intramuscular, intravenous, intrafootpad or intraperitoneal injection 1-several times or transplantation of an immunogen. Generally, immunization is performed 1-4 times every about 1-14 days from the initial immunization, and the antibody producing cell is obtained from the spleen etc. of the immunized mammal about 1-5 days from the final immunization.

A hybridoma (fusion cell) that secretes monoclonal antibody can be prepared by the method of Köhler and Milstein et al. (Nature, Vol. 256, p. 495-497, 1975) and a modified method according thereto. That is, hybridoma is obtained by cell fusion of antibody producing cells contained in the spleen, lymph node, bone marrow, tonsil etc., preferably spleen, the obtained from a mammal immunized as mentioned above, and myeloma cells free of an autoantibody producing ability, which are derived from a mammal preferably mouse, rat, guinea pig, hamster, rabbit, human and the like, more preferably mouse, rat or human.

Examples of the myeloma cells to be used for cell fusion include myeloma P3/X63-AG8.653 (653; ATCC No.CRL1580), P3/NSI/1-Ag4-1 (NS-1), P3/X63-Ag8.U1 (P3U1), SP2/0-Ag14 (Sp2/0, Sp2), PAI, F0 or BW5147 derived from mouse, myeloma 210RCY3-Ag.2.3. derived from rat, myeloma U-266AR1, GM1500-6TG-A1-2, UC729-6, CEM-AGR, D1R11 or CEM-T15 derived from human.

A hybridoma producing a monoclonal antibody can be screened for by culturing the obtained hybridoma in, for example, a microtiter plate, measuring the reactivity of the culture supernatant, in the well showing growth, to the polypeptide of the present invention used for the aforementioned immunization and the reactivity of the aforementioned supernatant to a carrier protein, by, for example, an immunoassay method such as ELISA and the like, and comparing them.

A hybridoma cloned by screening is cultured in a medium (e.g., DMEM containing 10% bovine calf serum). The centrifuged supernatant of the culture medium can be used as a monoclonal antibody solution. By injecting the hybridoma into the abdominal cavity of an animal from which the hybridoma is derived, ascites is produced in the animal, and the ascites obtained from the animal can be used as a monoclonal antibody solution. Monoclonal antibody is preferably isolated and/or purified by a method similar to that of the aforementioned polyclonal antibody.

Chimeric antibody can be produced by reference to, for example, JP-B-3-73280 and the like, humanized antibody can be produced by reference to, for example, JP-A-4-506458, JP-A-62-296890 and the like, and human antibody can be produced by reference to, for example, "Nature Genetics, Vol. 15, p. 146-156, 1997", "Nature Genetics, Vol. 7, p. 13-21, 1994", JP-A-4-504365, WO 94/25585, "Nature, Vol. 368, p. 856-859, 1994", JP-A-6-500233 and the like.

An antibody by phage display can be produced by, for example, recovering and concentrating a phage having affinity for antigen by biopanning from a phage library prepared for screening human antibody, whereby antibody such as Fab and the like, and the like can be obtained easily. In this case, the antibody library is preferably screened using the polypeptide of the present invention as an antigen. As a preferable antibody library and screening method of antibody, "Science, 228: 4075 p. 1315-1317 (1985)", "Nature, 348: p. 552-554 (1990)", "Curr. Protein Pept. Sci., 1(2): p. 155-169 (2000)", WO 01/062907 and the like can be referred to. An antibody can be prepared using an antibody fragment obtained thereby or utilizing DNA that the phage has.

The amount of the aforementioned antibody in the prophylactic or therapeutic agent of the present invention is not particularly limited as long as the above-mentioned effect can be afforded. It is generally 0.001-90 wt %, preferably 0.005-50 wt %, more preferably 0.01-10 wt %, of the whole prophylactic or therapeutic agent of the present invention.

The prophylactic or therapeutic agent of the present invention may contain a pharmaceutically acceptable carrier besides the aforementioned antibody as the active ingredient. As such carrier, a carrier generally used in the pharmaceutical field can be used. Examples thereof include, but are not limited to, excipients such as sucrose, starch, mannit, sorbit, lactose, glucose, calcium phosphate, calcium carbonate and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline and the like, basewaxes such as glycerol, polyethylene glycol and the like, and the like.

Examples of the administration dosage form of the prophylactic or therapeutic agent of the present invention include, but are not limited to, liquid, injection preparation and the like. The dosage form of the prophylactic or therapeutic agent of the present invention may be a controlled-release preparation such as an immediate-release preparation, a sustained-release preparation and the like. Since antibody is generally soluble in aqueous solvents, it is easily absorbed in any of the above-mentioned dosage forms. It is also possible to further increase the solubility of the antibody by a method known per se.

The prophylactic or therapeutic agent of the present invention that can be used for the prophylaxis, treatment or alleviation of disease involving IL-17A as an aggravation factor can be produced using the above-mentioned antibody as an active ingredient according to a means known per se as a preparation production method.

For example, the prophylactic or therapeutic agent of the present invention preferable for systemic administration can be produced by dissolving an effective amount of the antibody of the present invention in an aqueous or non-aqueous isotonic aseptic injection (e.g., injection preparation). It may be produced by freeze-drying the antibody of the present invention (e.g., freeze-dry preparation) and dissolving same in an aqueous or non-aqueous isotonic aseptic dilution solution. The prophylactic or therapeutic agent of the present invention preferable for topical administration can be produced by dissolving the antibody of the present invention in a dilution solution such as water and saline (e.g., liquid). The liquid can also be used for inhalation therapy into the bronchus, lung and the like by using a sprayer. These agents may contain antioxidant, buffer, bacteriostatic agent, isotonicity agent and the like. These prophylactic or therapeutic agents of the present invention can be sealed in a unit dose or plural dose container such as ampoule or vial.

While the dose of the prophylactic or therapeutic agent of the present invention can be appropriately determined according to the activity, kind or the amount of the antibody contained as the active ingredient, subject of administration, administration route, age and body weight of the subject of administration, and the like, for example, the daily dose (effective amount) for an adult (body weight 60 kg) in the amount of the antibody is 0.1 mg-1000 mg, preferably 0.1 mg-500 mg, more preferably 0.1 mg-300 mg. The prophylactic or therapeutic agent of the present invention can be administered in one to several portions per day as necessary, and can also be administered in several days.

The prophylactic or therapeutic agent of the present invention can be used in combination with known prophylactic or therapeutic agents for the aforementioned disease involving IL-17A as an aggravation factor. Only one kind or plural kinds thereof may be used in combination. In the present specification, "combined use" means that the prophylactic or therapeutic agent of the present invention and known prophylactic or therapeutic agents for disease involving IL-17A as an aggravation factor are used in combination, and the use form thereof is not particularly limited. For example, it includes both administration of a pharmaceutical composition containing the prophylactic or therapeutic agent of the present invention and known prophylactic or therapeutic agents for a disease involving IL-17A as an aggravation factor, and administration thereof, which are separately formulated without mixing, simultaneously or in a staggered manner.

EXAMPLES

The present invention is explained in more detail in the following by referring to Examples. The present invention is not limited thereby.

Experimental Example 1

Production of DNA Vaccine

DNA Vaccine Vector

To isolate hepatitis B virus core antigen (HBc), plasmid pPLc3 (Accession number LMBP 2470) was purchased from BCCM/LMBP Plasmid Collection. The following primers were designed and synthesized (WO 2012/141280).

HBcF 5'-gcc atg gat atc gat cct tca tat aaa gaa ttc gga gc-3' (SEQ ID NO: 3)

HBcR 5'-ggc ctc tca cta aca ttg aga ttc ccg aga ttg aga-3' (SEQ ID NO: 4)

Using the above-mentioned primer set, HBc was amplified by PCR.

Figure 1:
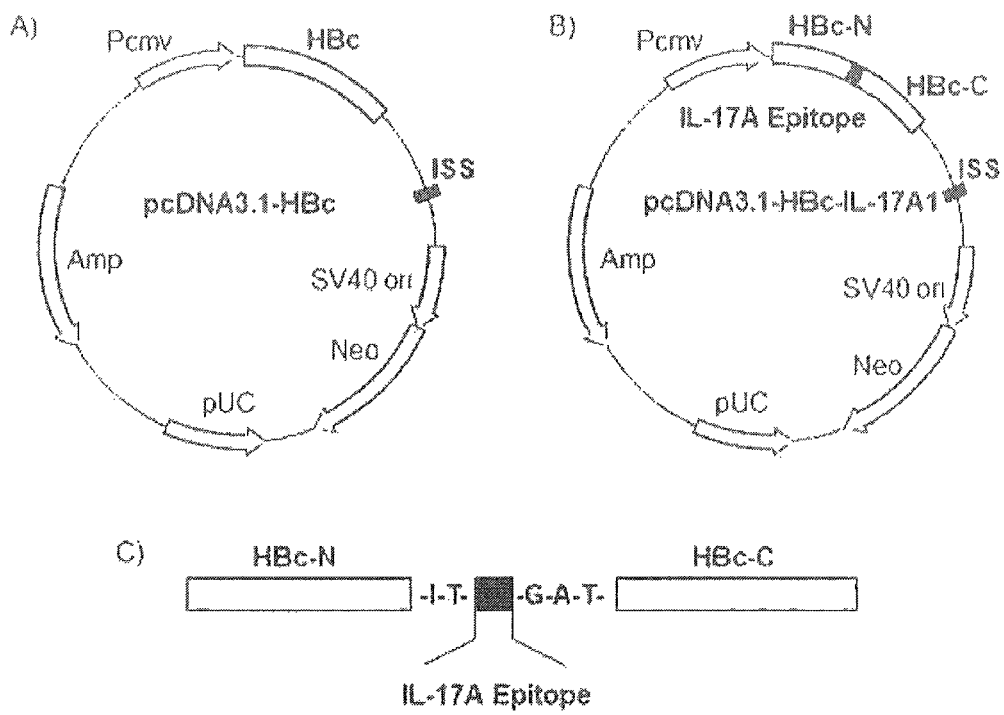
FIG. 1 shows the structures of expression vectors containing IL-17A epitope. A) is the structure of pcDNA3.1+ HBc vector, B) is the structure of a vector wherein a sequence encoding a spacer and a partial sequence of IL-17A is inserted between the 240th and 241st bases of Hbc, C) is a schematic showing of the vector wherein IL-17A epitope is inserted, as shown in the aforementioned B.

HBc obtained as mentioned above was cloned to pcDNA 3.1/V5-His TOPO TA Expression Kit (Invitrogen). Nucleic acid sequences encoding two kinds of epitope A1 and epitope A2 of the following mouse IL-17A were respectively inserted into pcDNA3.1-HBc vector by mutagenesis. In the following Examples, unless particularly indicated, a vaccine containing pcDNA3.1-HBc vector inserted with a nucleic acid sequence encoding mouse IL-17A1 epitope is indicated as IL-17A1 DNA vaccine, and a vaccine containing pcDNA3.1-HBc vector inserted with a nucleic acid sequence encoding mouse IL-17A2 epitope is indicated as IL-17A2 DNA vaccine. The structures of the vectors are shown in FIG. 1.

mouse IL-17A1 epitope RPSDYLNR (SEQ ID NO: 5)
mouse IL-17A2 epitope DHHMNSV (SEQ ID NO: 7)

Experimental Example 2

Administration of DNA Vaccine to Mouse

A DNA vaccine was injected with a syringe to femoral muscle of each of 6-week-old male mice below 3 times (120 µg/60 µl×1 site/administration) every 2 weeks by electroporation.

Experiment 1

Figure 4:
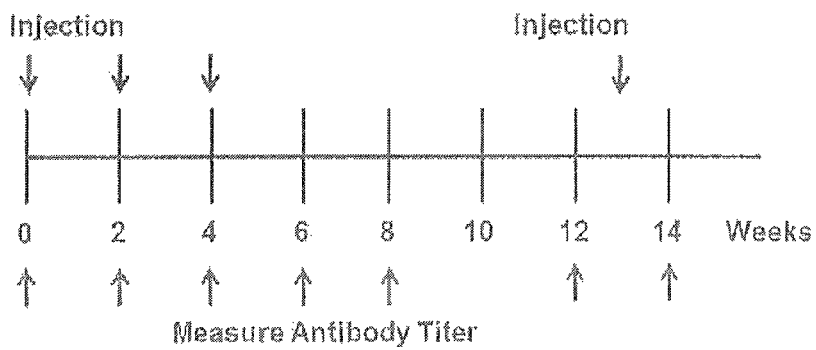
FIG. 4 shows A) a plan of IL-17A1 DNA vaccine administration to NZBWF1 mouse. B) shows an increase in the antibody titer of IL-17A1 DNA vaccine administration group.
Figure 4:
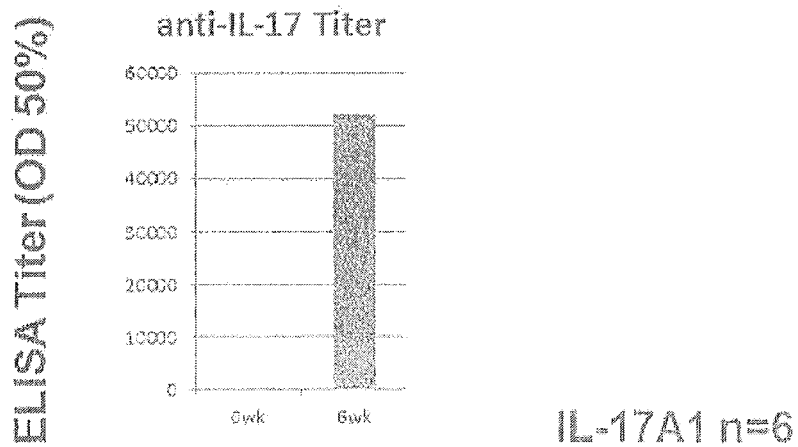

Measurement of Antibody Titer, Measurement of Various Cytokines in Blood or Urine, Analysis of Survival Rate NZBWF1 mouse (SLE disease model)
HBc-IL-17A1 (IL-17A1 DNA vaccine) group: 6 mice
HBc (pcDNA3.1-HBc vector) group: 6 mice
Saline group: 10 mice
The body weight was measured every week, and the serum was collected every 4 weeks.
The administration plan is shown in FIG. 4A.
MRL/lpr mouse (SLE disease model)
HBc-IL-17A1 (IL-17A1 DNA vaccine) group: 9 mice
Saline group: 9 mice
The body weight was measured every week, and the serum was collected every 4 weeks.

Experiment 2

Measurement of Antibody Titer, Analysis of Each Organ

MRL/lpr mouse
HBc-IL-17A1 (IL-17A1 DNA vaccine) group: 6 mice
Saline group: 6 mice
The body weight was measured every week, and the serum was collected every 4 weeks.

Example 1

Antigenicity of Mouse IL-17A Peptide

Measurement of Anti-IL-17A Antibody Titer by ELISA

Production of plate: Mouse IL-17A1 epitope+BSA conjugate and mouse IL-17A2 epitope+BSA conjugate were dispensed to a 96 well plate at a concentration of 10 µg/ml, and stood at 4° C. overnight. Recombinant mouse IL-17A was dispensed to a 96 well plate at a concentration of 0.25 µg/ml and stood at 4° C. overnight.

The aforementioned plate was washed once with PBS (200 µl), and blocked with 5% skim milk in PBS for 2 hr. The primary antibody (mouse antiserum) was serially diluted with 5% skim milk in PBS, applied by 50 µl to a 96 well plate, and incubated at 4° C. overnight.

The aforementioned plate was washed 7 times with PBS-T (0.05% Tween) (200 µl), the secondary antibody (anti-mouse IgG Ab-HRP-labeled) was diluted 1/1000 (5% skim milk), added by 50 µl, and incubated at ambient temperature for 3 hr. The plate was washed 3 times with PBS-T (0.05% Tween) (200 µl), TMB solution (50 µl) was added, shaded and incubated at ambient temperature for 30 min. 0.5N $H_2SO_4$ (50 µl) was added to discontinue the reaction and absorbance was measured at 450 nm.

Figure 3:
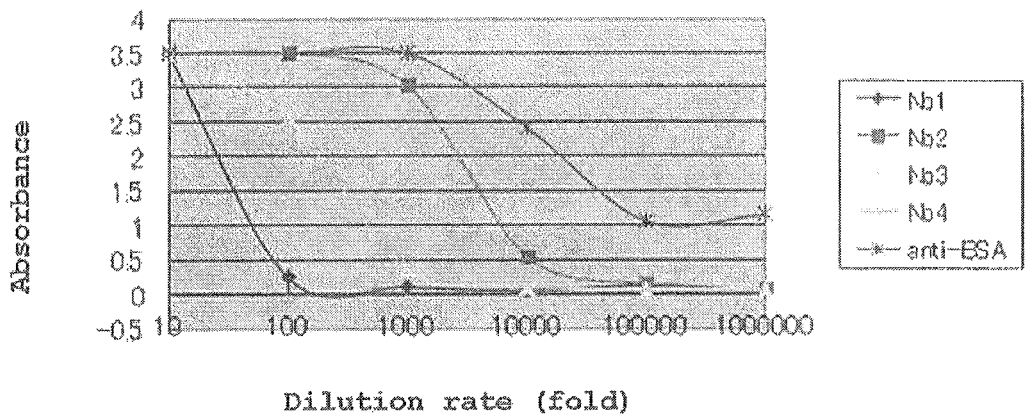
FIG. 3 shows an increase in the antibody titer of BALB/c mouse immunized with IL-17A1 DNA vaccine on week 6. The primary antibodies (mouse antisera) No1-No4 were diluted 10-fold and then serially diluted by 10-fold and used. No1: IL-17A1 No1 antisera, No2: IL-17A1 No2 antisera, No3: IL-17A1 No3 antisera, No4: IL-17A1 No4 antisera
Figure 5:
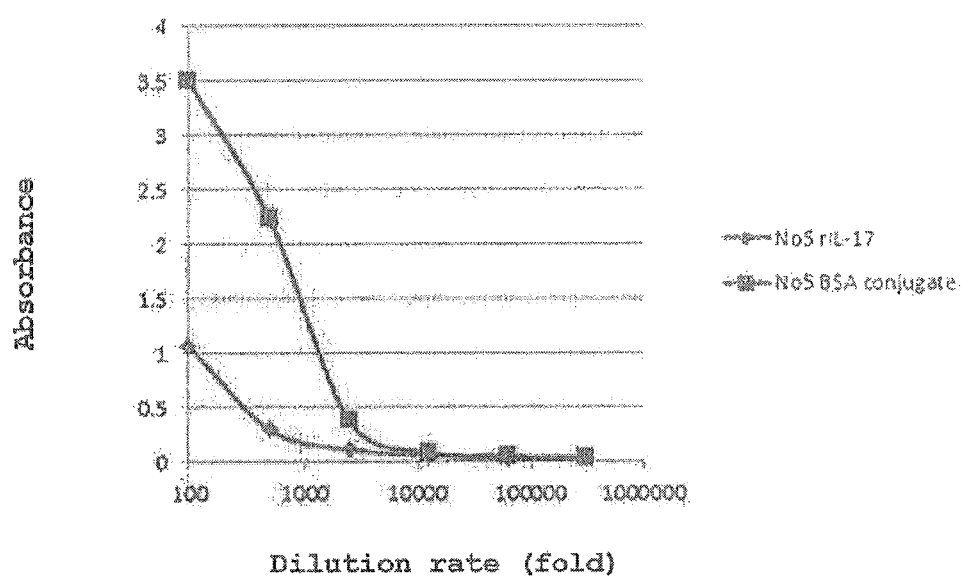
FIG. 5 shows a bond between an antiserum obtained from a mouse immunized with IL-17A1 DNA vaccine and BSA-IL-17A1 (RPSDYLNR) conjugate (No5 BSA conjugate) or mouse recombinant IL-17A (No5 rIL-17). The primary antibody (mouse antiserum) was diluted 100-fold, and then serially diluted by 5-fold and used.
Figure 7:
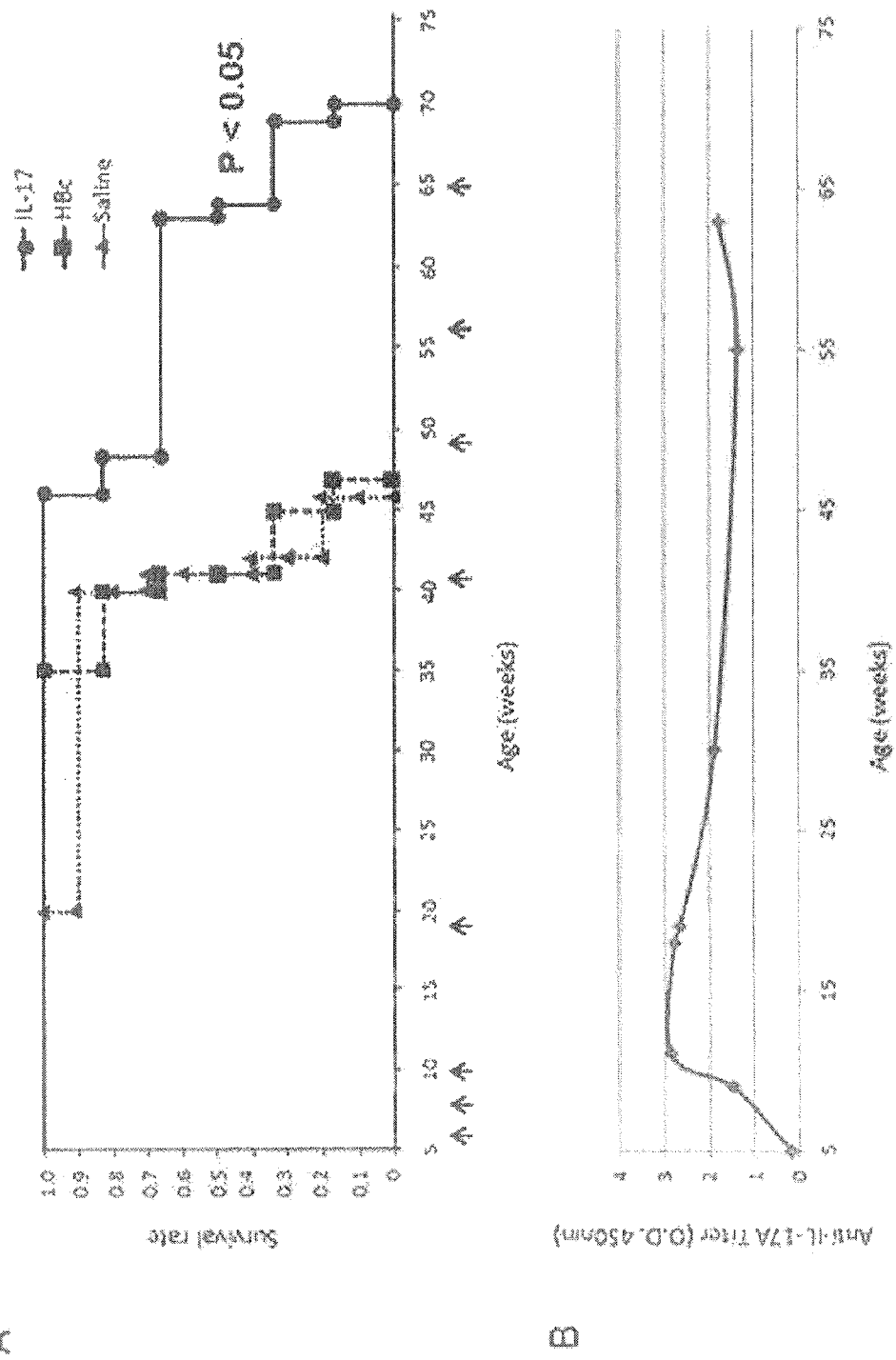
FIG. 7 shows A) survival rate of NZBWF1 mouse administered with IL-17A1 DNA vaccine (in the Figure, arrow means vaccine administration), and B) anti-IL-17A1 antibody titer.

In a preliminary experiment including immunization of BALB/c mouse with IL-17A1 DNA vaccine or IL-17A2 DNA vaccine, BALB/c mouse administered with IL-17A1 DNA vaccine showed an increase in the antibody titer (FIG. 3). According to the administration plan shown in FIG. 4A, IL-17A1 DNA vaccine was administered to NZBWF1 mouse. As a result, an increase in the antibody titer was found on week 6 (FIG. 4B), whereby production of an antibody that correctly recognizes recombinant mouse IL-17A was confirmed (FIG. 5). Furthermore, it was confirmed that the anti-IL-17A1 antibody titer is maintained for a long time (FIG. 7B).

Figure 2:
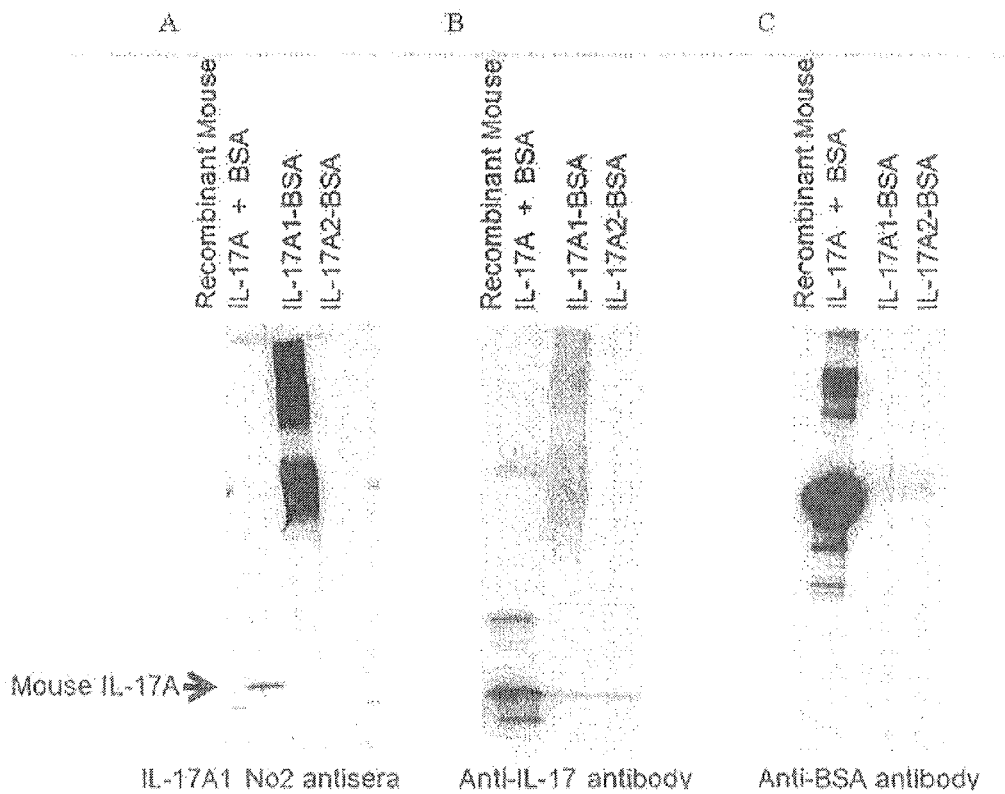
FIG. 2 shows a bond between recombinant IL-17A protein and an antibody derived from the serum of BALB/c mouse immunized with IL-17A1 DNA vaccine (epitope sequence: RPSDYLNR) or IL-17A2 DNA vaccine. A) Antiserum obtained by administration of IL-17A1 DNA vaccine was used as the primary antibody. B) Anti-IL-17A antibody was used as the primary antibody. C) Anti-BSA antibody was used as the primary antibody.

Confirmation of Reactivity of Anti-Mouse IL-17A Antibody with Recombinant Mouse IL-17A by Western Blotting According to a conventional method, a protein was applied to each lane and electrophoresis was performed. After the electrophoresis, the protein was transferred to a membrane. After blocking, each primary antibody was added and the membrane was incubated at 4° C. overnight. Then, the secondary antibody was reacted, and the binding of the antibody was detected by color developing reaction. The results are shown in FIG. 2.

lane 1: recombinant mouse IL-17A
lane 2: mouse IL-17A1 epitope+BSA conjugate
lane 3: mouse IL-17A2 epitope+BSA conjugate Primary Antibody A: antiserum of BALB/c mouse administered with IL-17A1 DNA vaccine
B: commercially available anti-mouse IL-17A antibody
C: commercially available anti-BSA antibody The antiserum of mouse administered with IL-17A1 DNA vaccine was bound to recombinant mouse IL-17A in the same manner as commercially available anti-mouse IL-17A antibody.

The antiserum of mouse administered with IL-17A1 DNA vaccine specifically recognized mouse IL-17A1 epitope+BSA conjugate, and did not react with mouse IL-17A2 epitope+BSA conjugate.

The recombinant mouse IL-17A was stabilized by adding a large amount of BSA, and commercially available anti-BSA antibody recognize same as well as mouse IL-17A1 epitope+BSA conjugate and mouse IL-17A2 epitope+BSA conjugate.

Example 2

Figure 6:
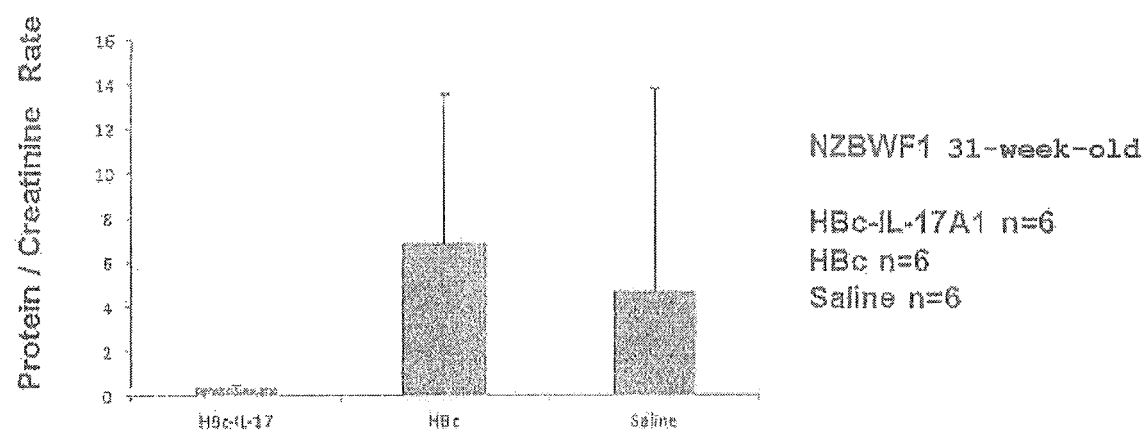
FIG. 6 shows A) urine protein (NZBWF1 mouse), B) urine MCP-1 concentration (pg/ml) (NZBWF1 mouse), C) blood IL-17A concentration (pg/ml) (NZBWF1 mouse), D) blood TNF-α concentration (pg/ml) (MRL/lpr mouse), E) blood IL-1β concentration (pg/ml) (NZBWF1 mouse) and F) blood TNF-α concentration (pg/ml) (NZBWF1 mouse), of NZBWF1 mouse or MRL/lpr mouse administered with IL-17A1 DNA vaccine.
Figure 1:
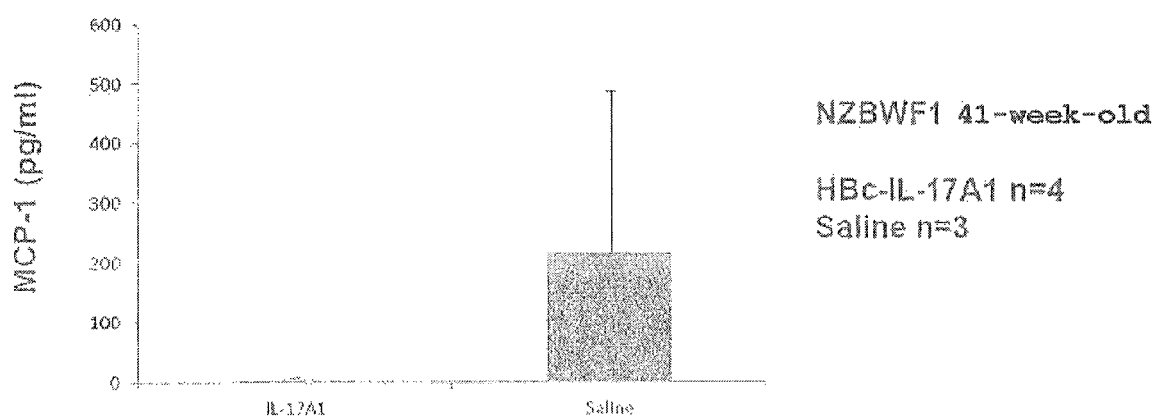
Figure 8:
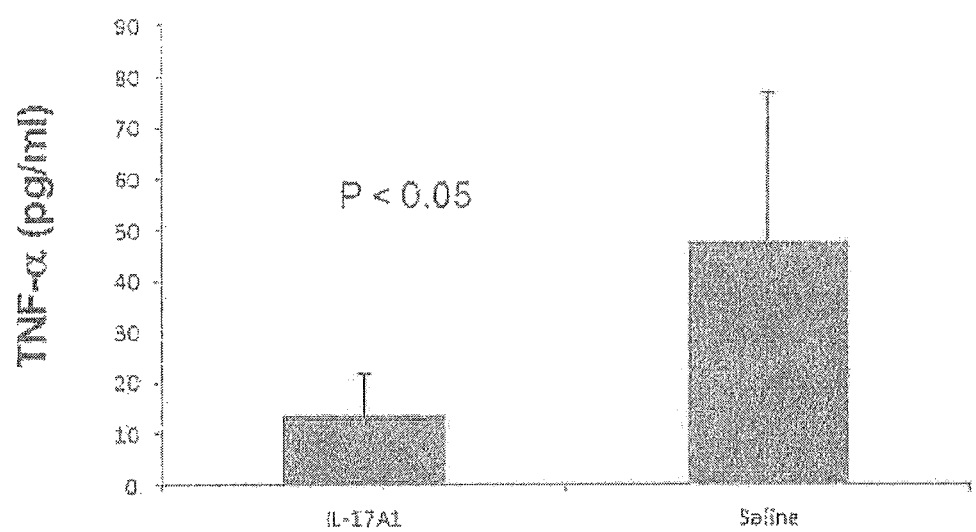
FIG. 8 shows A) blood TNF-α concentration (pg/ml) and B) survival rate (in the Figure, arrow means vaccine administration), of MRL/lpr mouse administered with IL-17A1 DNA vaccine.
Figure 8:

Effect of IL-17A Vaccine on SLE Model Mouse
Measurement of Blood IL-1β, TNF-α and IL-17A
Concentration, Concentration of MCP-1 in Urine Using Quantikine ELISA kit and in accordance with the protocol specified by the manufacturer, the concentration of IL-1β, TNF-α, IL-17A and MCP-1 was measured. Serum was used by 25 μl. Urine was used by 50 μl. Using the standard sample attached to the kit, an analytical curve was drawn, and each cytokine concentration was quantified. A significant decrease in blood IL-1β was found in NZBWF1 mouse IL-17A1 DNA vaccine administration group (FIG. 6E). The blood IL-17A concentration, concentration of MCP-1 in urine and blood TNF-α concentration showed a tendency toward a decrease (FIG. 6C, B, F). A significant decrease in TNF-α was also found in the MRL/lpr mouse IL-17A1 DNA vaccine administration group described in Experiment 1 (FIG. 6D, 8A).

Qualitative Examination of Urine urine was occasionally collected from mouse under anesthesia. Using a urine multistix test strip, urine protein, urine creatinine, urine albumin, urine occult blood, urine specific gravity and the like were measured. The NZBWF1 mouse IL-17A1 DNA vaccine administration group showed a tendency toward a decrease in urine protein (FIG. 6A).

Survival Rate

After administration of IL-17A1 DNA vaccine to NZBWF1 mouse, which is SLE model mouse, the mouse was observed every day, and the day when the mouse died was recorded. The number of dead mice was added every week, and a survival rate graph was formed. As a result of long-term observation of the IL-17A1 DNA vaccine administration group, a significant elongation of the survival period of the vaccine administration group was found (FIG. 7A). In addition, a life prolonging tendency was also found in the MRL/lpr mouse DNA vaccine administration group described in Experiment 1 (FIG. 8B).

Organ Weight Analysis

Figure 9:
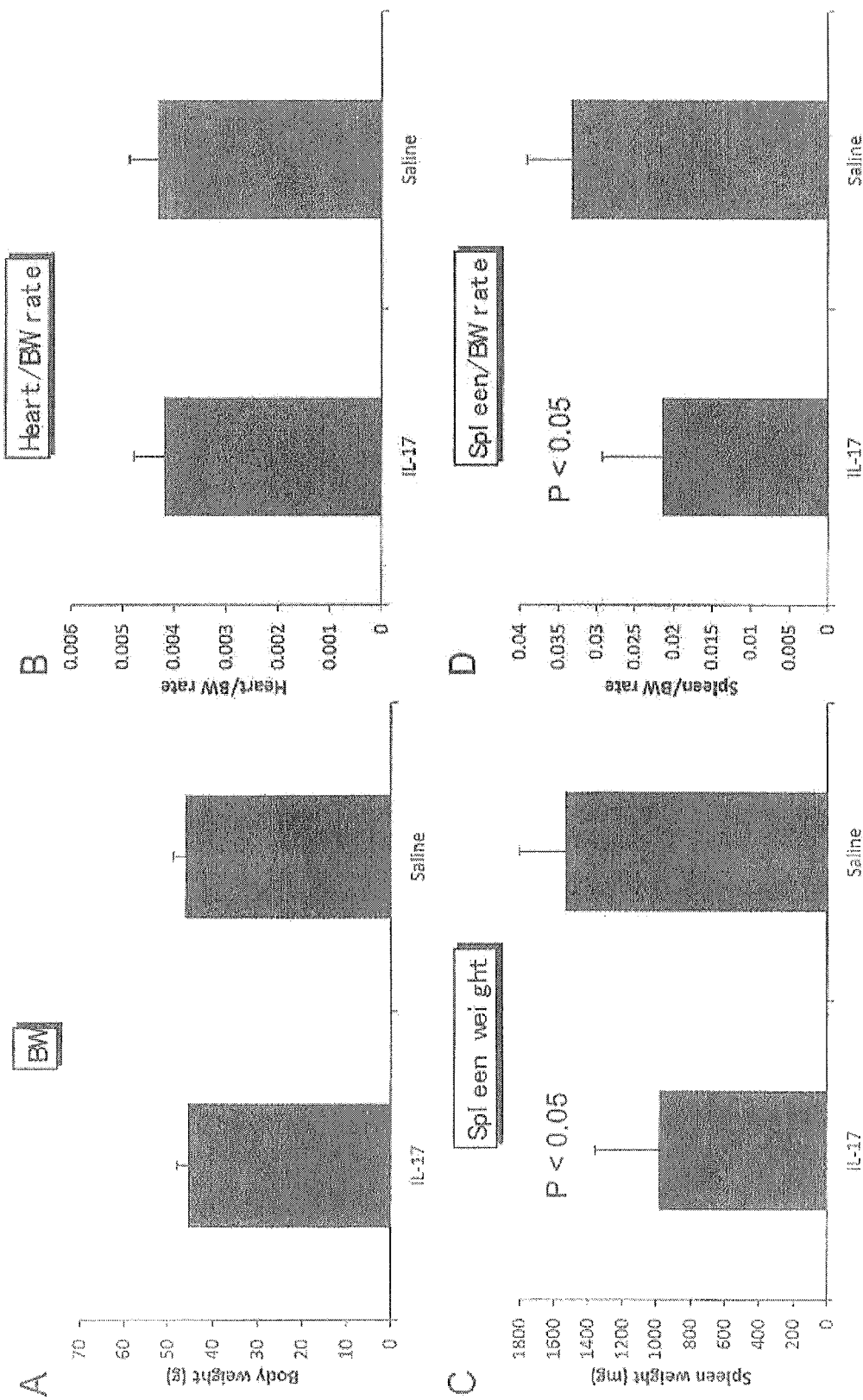
FIG. 9 shows A) body weight (g), B) proportion of heart weight per total body weight, C) spleen weight (mg) and D) spleen weight per total body weight, of MRL/lpr mouse administered with IL-17A1 DNA vaccine.

After administration of IL-17A1 DNA vaccine to MRL/lpr mouse described in Experiment 2, changes in the organ weight were examined. A significant difference in the body weight was not found between two groups of HBc-IL-17A1 group and Saline group (FIG. 9A). As a control, the heart weight per total body weight was measured, but a significant difference was not found (FIG. 9B). On the other hand, the spleen weight showed a significant decrease after administration of IL-17A1 DNA vaccine (FIG. 9C). Also, the spleen weight per total body weight showed a significant decrease (FIG. 9D). enlarged spleen was found in SLE patients, an increase in spleen weight per total body weight in these model mice reflects aggravation of SLE. It was clarified from the results that IL-17A1 DNA vaccine has a treatment effect on SLE.

Statistical Method

The survival rate was statistically processed by the Kaplan-Meier method.

Figure 10:
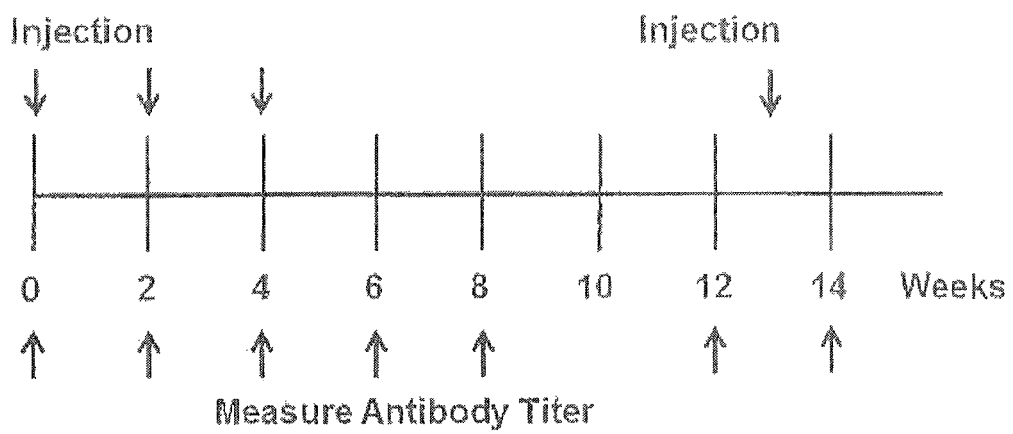
FIG. 10 shows the analysis plan of histopathology. A) shows a plan of IL-17A1 DNA vaccine, Saline administration to NZBWF1 mouse, and B) shows a plan of IL-17A1 DNA vaccine, Saline administration to MRL/lpr mouse.
Figure 10:
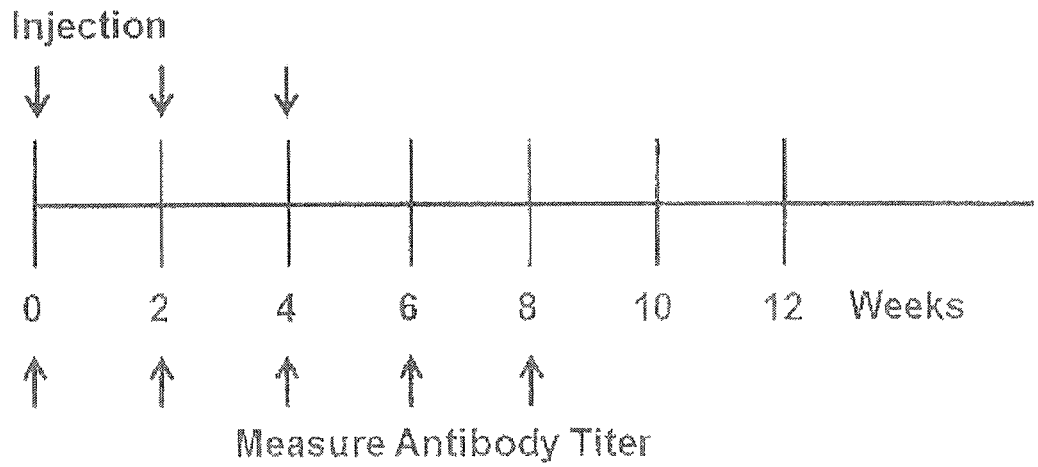

The analysis plan of histopathology is shown in FIG. 10.

Experiment 3

NZBWF1 mouse
HBc-IL-17A1 (IL-17A1 DNA vaccine) group: 9 mice
Saline group: 9 mice
The body weight was measured every week, and the serum was collected every 4 weeks.

MRL/lpr mouse
HBc-IL-17A1 (IL-17A1 DNA vaccine) group: 9 mice
Saline group: 9 mice
The body weight was measured every week, and the serum was collected every 4 weeks.

Tissue Staining

In immunohistochemistry analysis, each isolated organ was fixed in 4% paraformaldehyde for 24 hr and embedded in paraffin, and cut into 4 μm sections. The sections were reacted with primary antibody (anti-F4/80 antibody) and the secondary antibody (HRP-labeled anti-rat IgG antibody). Slides were finally counterstained with haematoxylin and subjected to microscopic observation. In histological examination assay, the kidney, submandibular gland and liver were dissected, fixed in 4% paraformaldehyde overnight and embedded in paraffin. The 4 μm section of kidney was stained with PAS. The 4 μm sections of submandibular gland and liver were stained with HE.

Kidney

Figure 11:
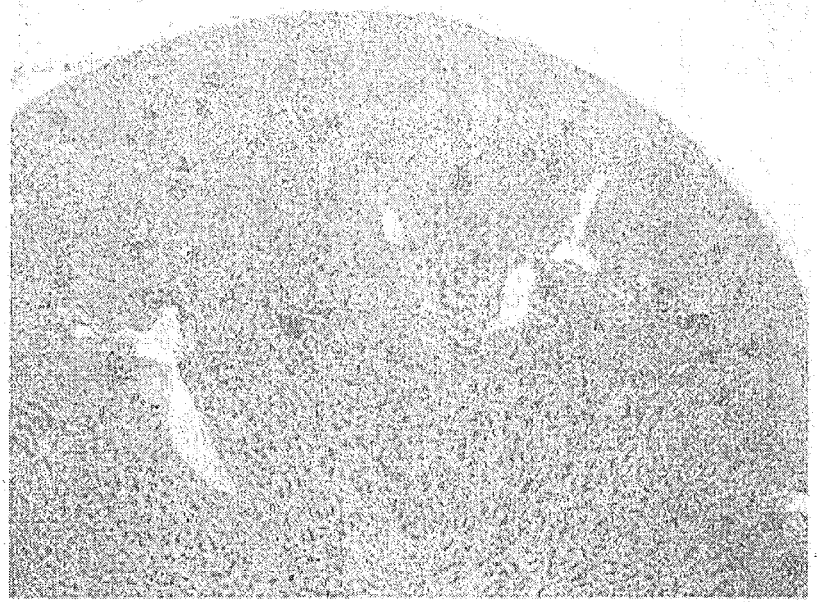
FIG. 11 shows A) photograph (mildly enlarged) of PAS staining, B) photograph (highly enlarged) of PAS staining, C) photograph of F4/80 immunostaining (NZBWF1 mouse), D) photograph of F4/80 immunostaining (MRL/lpr mouse), of the kidney of NZBWF1 mouse or MRL/lpr mouse after administration of IL-17A1 DNA vaccine or Saline.
Figure 1:
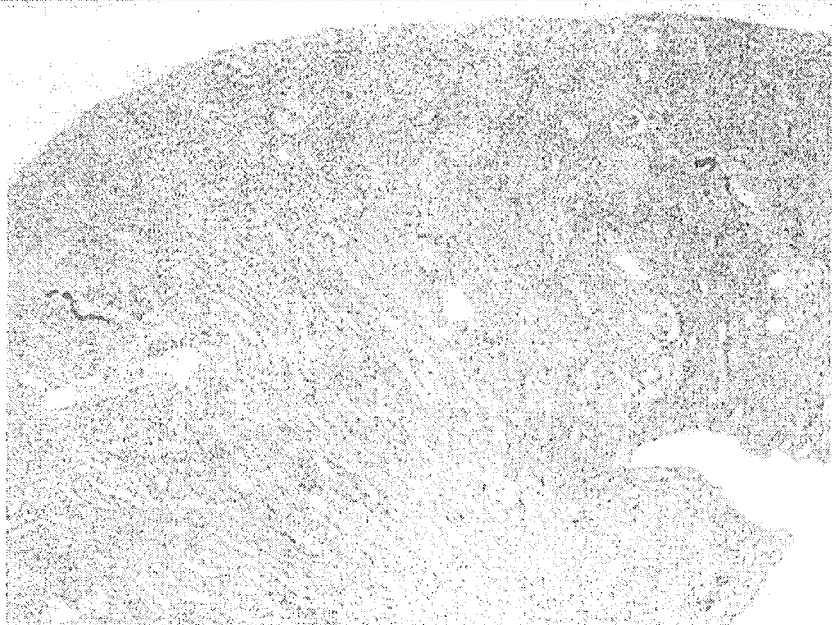
Figures 2, 11:
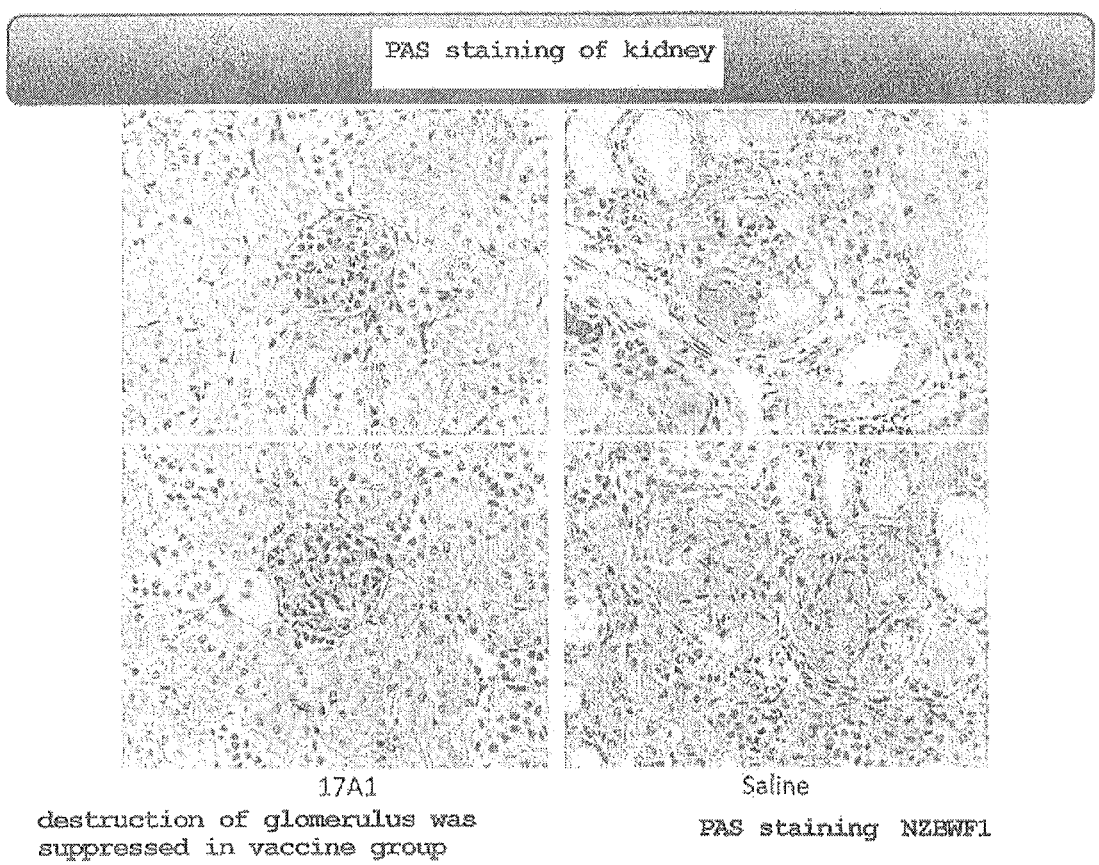
Figure 11:
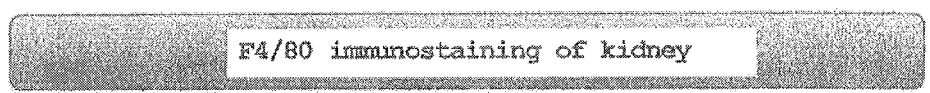
Figure 3:
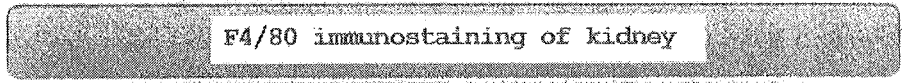

The level of kidney lesion in NZBWF1 mouse or MRL/lpr mouse was confirmed by PAS staining. The results are shown in FIG. 11A, B. Destruction of glomerulus and stroma was suppressed in the vaccine administration group. The level of infiltration of macrophage was confirmed by F4/80 immunostaining. The results are shown in FIG. 11C, D. Infiltration of macrophage into glomerulus periphery and stroma was suppressed in the vaccine administration group.

Submandibular Gland

Figure 12:
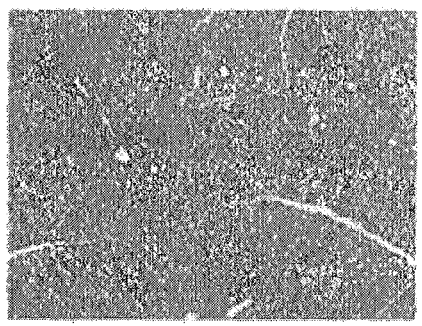
FIG. 12 shows photographs of HE staining of submandibular gland after administration of IL-17A1 DNA vaccine or Saline to NZBWF1 mouse.
Figure 12:
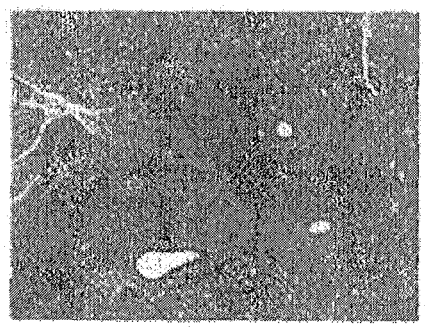

The level of submandibular gland inflammation in NZBWF1 mouse was confirmed by HE staining. The results are shown in FIG. 12. Suppression of submandibular gland inflammation was found in the vaccine administration group.

Liver

Figure 13:
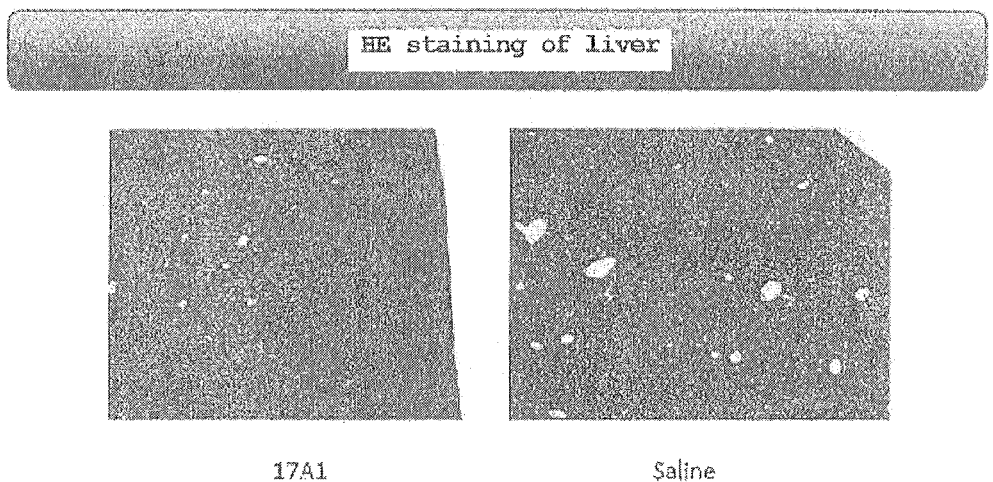
FIG. 13 shows photographs of HE staining of liver after administration of IL-17A1 DNA vaccine or Saline to NZBWF1 mouse or MRL/lpr mouse.
Figure 13:
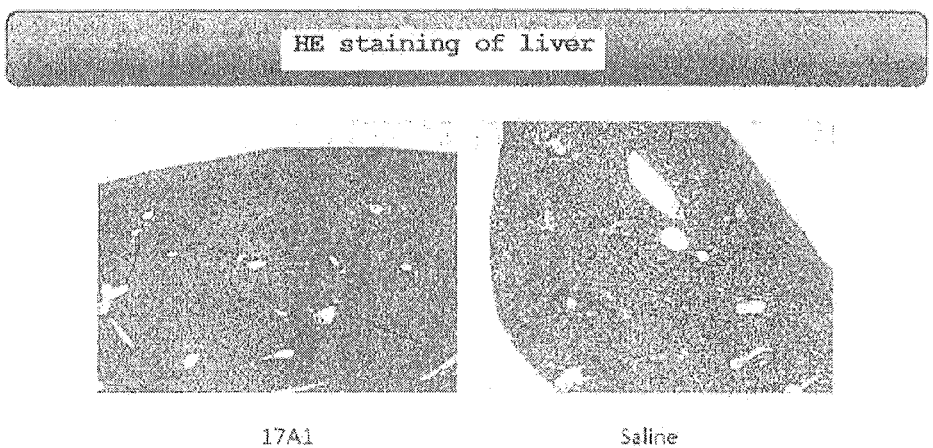

To confirm safety of the vaccine, tissue section of the liver was subjected to HE staining and observed. The results are shown in FIG. 13. The absence of pathological findings was confirmed in the vaccine administration group and Saline administration group of any mouse of NZBWF1 mouse (FIG. 13A) and MRL/lpr mouse (FIG. 13B).

Example 3

Effect of IL-17A Vaccine on Colitis Model Mouse

Figure 14:
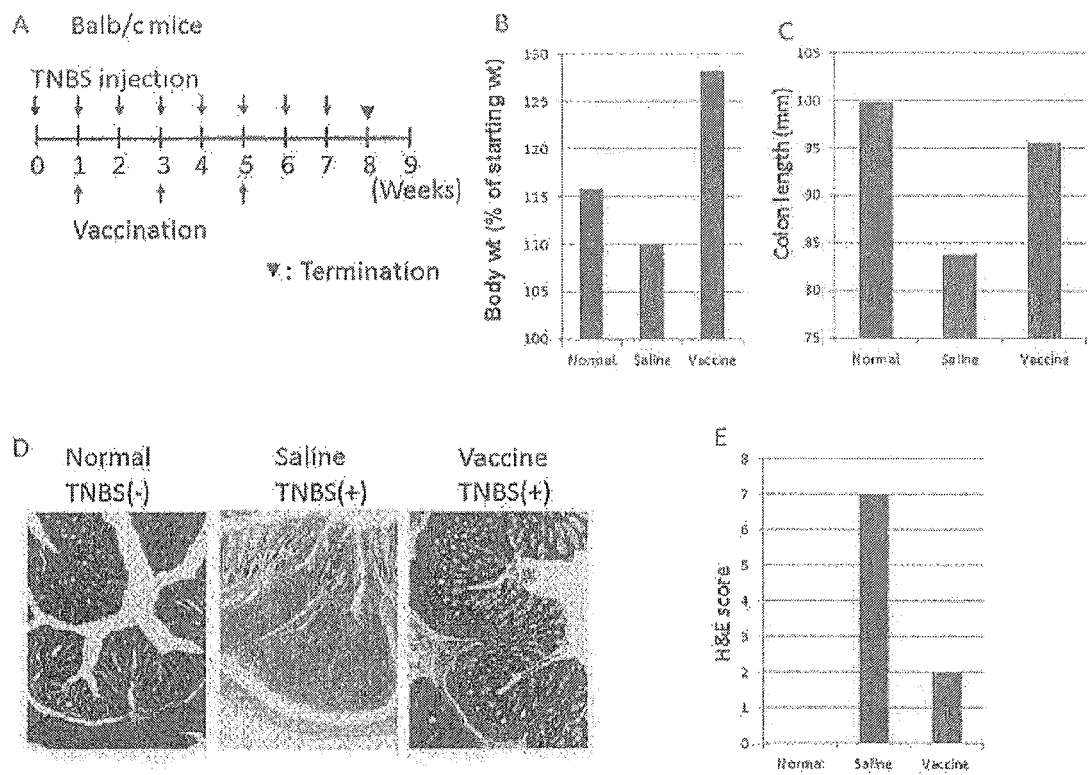
FIG. 14 shows A) a plan of TNBS administration and IL-17A1 DNA vaccine administration to BALB/c mouse. In addition, B) shows an increase (%) in body weight, C) shows length (mm) of large intestine, D) shows photographs of HE staining of large intestine and E) shows HE score of large intestine, of BALB/c mouse administered with TNBS and IL-17A1 DNA vaccine or Saline.

TNBS solution (2 mg/100 μl/injection) was injected into the intestine of 6-week-old male mice below and IL-17A1 DNA vaccine was administered 3 times (120 μg/60 μl×1 site/administration) every 2 weeks by electroporation. At week 8, the mice were sacrificed. The administration plan is shown in FIG. 14(A).

Experiment 4

BALB/c mouse
Normal group (TNBS(−)): 1 mouse
Vaccine group (HBc-IL-17A1 group; TNBS(+)): 3 mice
Saline group (TNBS(+)): 3 mice Body Weight Changes in the body weight of BALB/c mouse described in Experiment 4 were examined after 8 weeks from the TNBS administration. The amount of increase in the body weight of mouse decreased by the induction of colitis by TNBS (Saline group); however, the decrease effect was not found in the vaccine group (FIG. 14(B)).

Length of Large Intestine

The length of the large intestine of BALB/c mouse described in Experiment 4 was examined after 8 weeks from the TNBS administration. The length of the large intestine shortened by the induction of colitis by TNBS (Saline group); however, the effect was suppressed in the vaccine group (FIG. 14(C)).

Large Intestine

The large intestine of the sacrificed mouse was dissected, fixed overnight in 4% para-formaldehyde, and embedded in paraffin. A 4 μm section of the large intestine was subjected to HE staining and histologically examined. Saline group showed pathological finding such as infiltration of inflammatory cells and the like (FIG. 14(D)). Also, the pathological findings of HE-stained section were scored. A decrease in the H&E score was found in the vaccine group (FIG. 14(E)).

From the above results, IL-17A vaccine showed a suppressive effect on colitis in TNBS-induced colitis model mouse.

Example 4

Effect of IL-17A Vaccine on Arthritis Model Mouse

Figure 15:
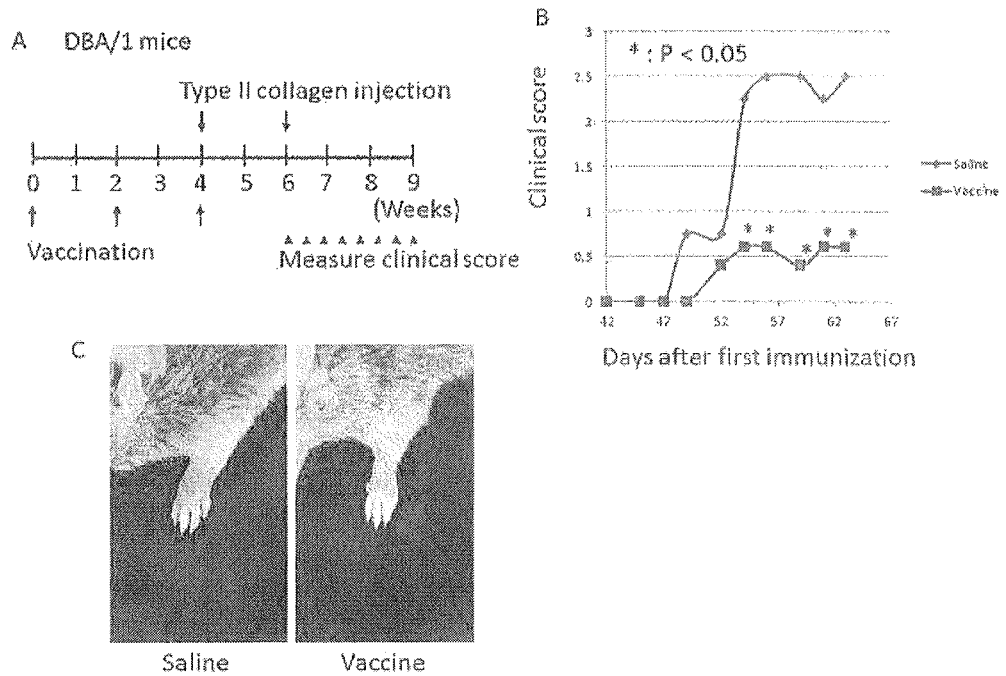
FIG. 15 shows A) a plan of IL-17A1 DNA vaccine administration and Type II collagen administration to DBA/1 mouse. In addition, B) shows clinical score of arthritis and C) shows photographs of joint of DBA/1 mouse administered with IL-17A1 DNA vaccine or Saline and Type II collagen.

A mouse IL-17A1 DNA vaccine was administered to femoral muscle of each of 6-week-old male mice below 3 times (120 μg/60 μl×1 site/administration) every 2 weeks by electroporation. Type II collagen and CFA (complete Freund's adjuvant) were administered at 28 days from the first vaccine administration, and Type II collagen and IFA (incomplete Freund's adjuvant) were administered at 42 days from the first vaccine administration to induce arthritis. Thereafter, the level of arthritis was observed 3 times per week and scored. The administration plan is shown in FIG. 15(A).

Experiment 5

DBA/1 mouse
Vaccine group (HBc-IL-17A1 group): 6 mice
Saline group (saline group): 6 mice Clinical Score The clinical score and clinical findings of arthritis, in DBA/1 mouse described in Experiment 5 were examined. It was found that the vaccine group shows a suppressive effect on the onset and progression of arthritis (FIG. 15(B), (C)).

From the above results, IL-17A vaccine showed a suppressive effect on arthritis in the model mouse with arthritis due to Type II collagen.

Example 5

Effect of IL-17A Vaccine on Colon Cancer Model Mouse

Figure 16:
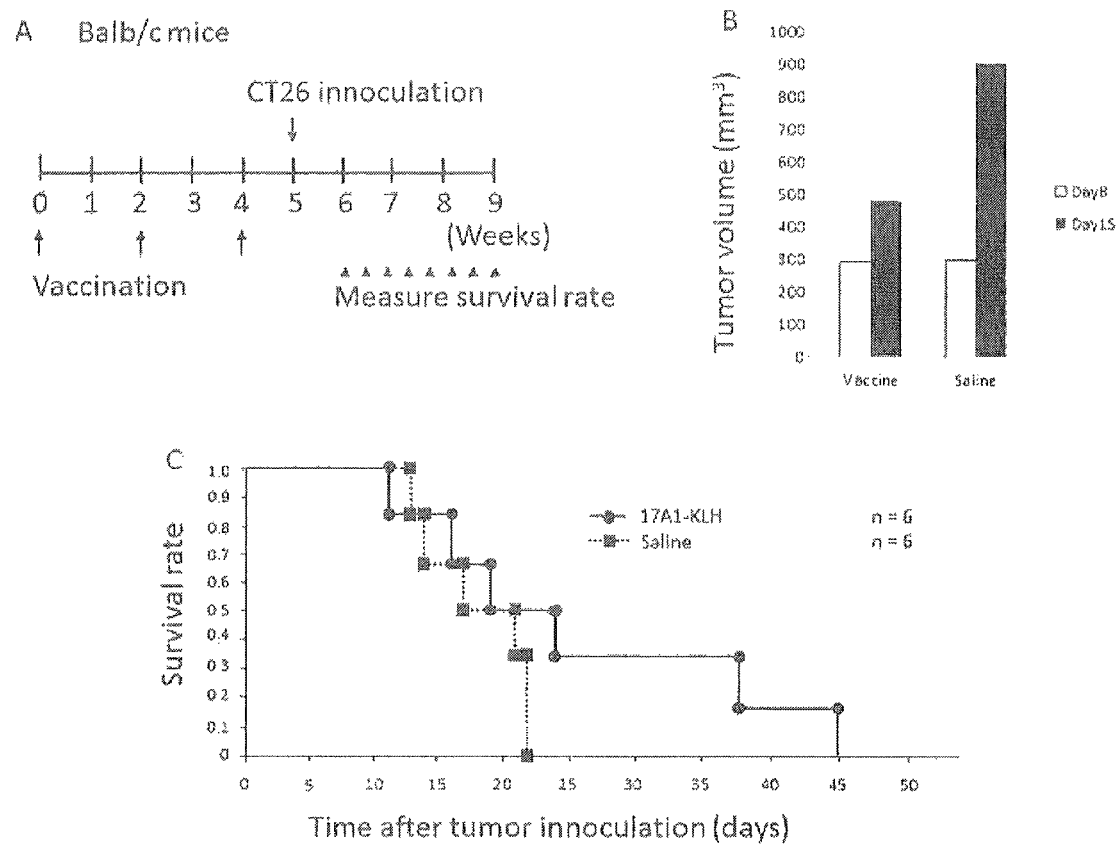
FIG. 16 shows A) a plan of IL-17A1 peptide vaccine administration and CT26 cell inoculation to BALB/c mouse. B) shows tumor volume (mm$^3$) and C) shows survival rate, of BALB/c mouse that underwent administration of IL-17A1 peptide vaccine or Saline, and CT26 cell inoculation.

A vaccine containing a peptide consisting of mouse IL-17A1 epitope (KLH conjugated) was administered to femoral muscle of each of 6-week-old male mice mentioned below 3 times (25 μg/25 μl+adjuvant 25 μl/administration) every 2 weeks (adjuvant was CFA for first administration, IFA for second and third administrations). Mouse colon cancer cell line CT26 cells ($5×10^5$ cells/Body) were inoculated at 5 weeks from the first vaccine administration. Thereafter, the tumor volume (0.5×major axis×minor axis×minor axis) was measured every week. The observation was continued until all mice died, and the survival period was confirmed. The administration plan is shown in FIG. 16(A).

Experiment 6

BALB/c Mouse

Vaccine group (IL-17A1-KLH group): 6 mice
Saline group (saline group): 6 mice

Tumor Volume

The tumor volume at 8 and 15 days from inoculation of CT26 cells to BALB/c mouse described in Experiment 6 was examined. It was found that the vaccine group has a suppressive effect on an increase in the tumor volume (FIG. 16(B)).

Survival Rate

CT26 cells were inoculated to BALB/c mouse administered with vaccine, the mouse was observed every day, and the day when the mouse died was recorded. As a result of long-term observation of the vaccine administration group, a significant elongation of the survival period was found (FIG. 16(C)).

From the above results, IL-17A vaccine showed a suppressive effect on tumor increase and a survival period elongation effect in the colon cancer model mouse due to the inoculation of CT26 cells.

Example 6

Effect of IL-17A Vaccine on Lung Cancer Model Mouse

Figure 17:
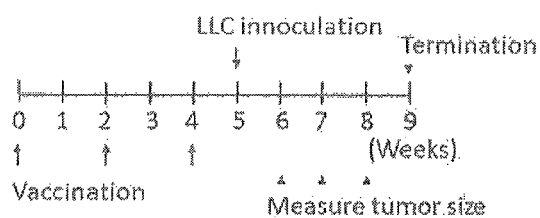
FIG. 17 shows A) a plan of IL-17A1 DNA vaccine administration and LLC cell inoculation to C57 BL/6 mouse. B) shows body weight (g), C) shows tumor volume (mm$^3$), D) shows tumor weight (mg) after 28 days from LLC cell inoculation, E) shows photographic image of lung metastasis, F) shows number (cancer) of lung metastasis and G) shows number (cancer) of liver metastasis, of C57 BL/6 mouse that underwent administration of IL-17A1 DNA vaccine or Saline, and LLC cell inoculation.
Figure 17:
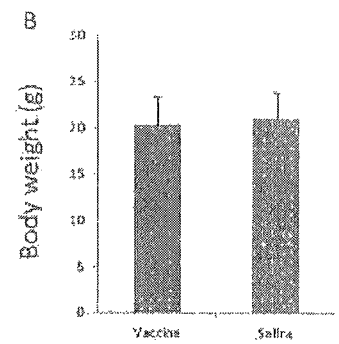
Figure 17:
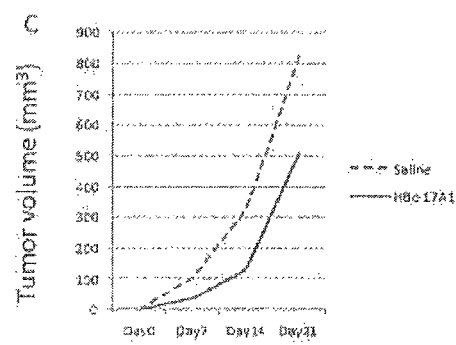
Figure 17:
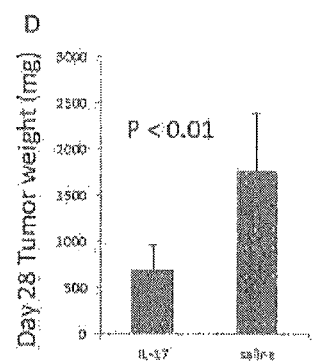
Figure 17:
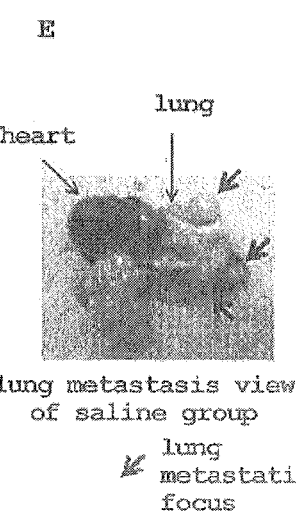
Figure 17:
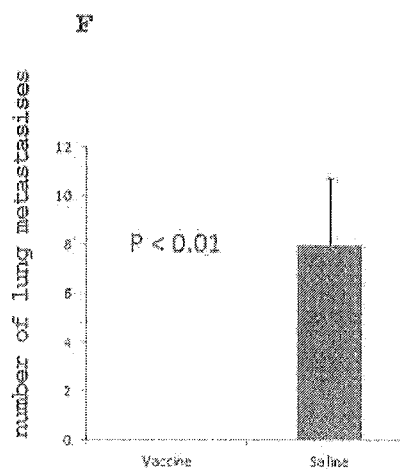
Figure 17:
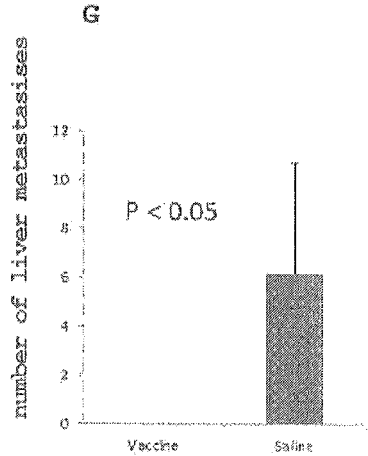

A mouse IL-17A1 DNA vaccine was administered to femoral muscle of each of 6-week-old male mice below 3 times (120 μg/60 μl×1 site/administration) every 2 weeks by electroporation. Mouse lung cancer cell line LLC cells ($5×10^5$ cells/Body) were inoculated at 5 weeks from the first vaccine administration. Thereafter, the tumor volume (0.5×major axis×minor axis×minor axis) was measured every week. At week 9, the mice were sacrificed, and tumor weight, lung metastasis and liver metastasis were confirmed. The administration plan is shown in FIG. 17(A).

Experiment 7

C57 BL/6 Mouse

Vaccine group (HBc-IL-17A1 group): 5 mice
Saline group (saline group): 5 mice
Body Weight The mouse described in Experiment 7 was sacrificed and the body weight was examined. The body weight of the mouse showed no significant difference between the both groups (FIG. 17(B)).
Tumor Volume LLC cell was inoculated to C57 BL/6 mouse described in Experiment 7, and the tumor volume was examined every week. It was found that the vaccine group has a suppressive effect on an increase in the tumor (FIG. 17(C)).
Tumor Weight The mouse described in Experiment 7 was sacrificed and the tumor weight was examined. The vaccine group was found to have a suppressive effect on an increase in the tumor weight (FIG. 17(D)).
Presence or Absence of Metastasis Lung metastasis and liver metastasis were not found in the vaccine group. In the vaccine non-administration group, lung metastasis was found (FIG. 17(E), (F), (G)).

From the above results, IL-17A vaccine showed a tumor increase suppressive effect and a metastasis suppressive effect in the model mouse with lung cancer caused by inoculation of LLC cell.

Example 7

Antigenicity of Human IL-17A Peptide

Measurement of Anti-IL-17A Antibody Titer by ELISA

A vaccine containing a peptide consisting of the following human IL-17A1 epitope (KLH conjugated) corresponding to mouse IL-17A1 epitope (RPSDYLNR (SEQ ID NO: 5)) was produced, and intradermally administered to BALB/c mouse 3 times at 2-week intervals. The serum antibody titer was measured at 6 weeks from the first administration according to the method described in Example 1.
human IL-17A1 epitope RSSDYYNR (SEQ ID NO: 1)

As a result, the antibody titer of BALB/c mouse administered with the vaccine increased (FIG. 18). The aforementioned serum also showed intersection reactivity with mouse IL-17A1 epitope (FIG. 19(A)). Furthermore, the serum obtained by the administration of a vaccine containing a peptide consisting of mouse IL-17A1 epitope also showed intersection reactivity with human IL-17A1 epitope (FIG. 19(B)).

In addition, a vaccine containing a peptide consisting of two kinds of epitopes (human IL-17A2 epitope, human IL-17A3 epitope) of the following human IL-17A (KLH conjugated) was produced, and intradermally administered to BALB/c mouse 3 times at 2-week intervals. The serum antibody titer was measured at 6 weeks from the first administration according to the method described in Example 1.
human IL-17A2 epitope ADGNVDYHMNSVPIQQE (SEQ ID NO: 8)
human IL-17A3 epitope LRREPPHCPNSFRL (SEQ ID NO: 9)

As a result, the antibody titer of BALB/c mouse administered with the vaccine containing a peptide consisting of human IL-17A2 epitope increased (FIG. 20).

Furthermore, a vaccine containing a peptide consisting of the following human IL-17A4, which is a partial sequence of human IL-17A1 epitope (KLH conjugated), was produced. In addition, a vaccine containing a DNA encoding human IL-17A5, human IL-17A6 or human IL-17A7, which is a partial sequence of human IL-17A1 epitope, was produced according to Experimental Example 1, and intradermally administered to BALB/c mouse 3 times at 2-week intervals. The serum antibody titer was measured at 6 weeks from the first administration according to the method described in Example 1.
human IL-17A4 epitope SDYYN (SEQ ID NO: 11)
human IL-17A5 epitope SDYY (SEQ ID NO: 12)
human IL-17A6 epitope SDY
human IL-17A7 epitope DYY As a result, the antibody titer of BALB/c mouse administered with the vaccine containing a peptide consisting of human IL-17A4 epitope or the vaccine containing a DNA encoding human IL-17A5 epitope, human IL-17A6 epitope or human IL-17A7 epitope increased (FIG. 21).

Example 8

Effect of Human IL-17A Vaccine on Arthritis Model Mouse

A vaccine containing a peptide consisting of human IL-17A1 epitope, human IL-17A2 epitope or human IL-17A4 epitope was administered to femoral muscle of each of the following 6-week-old male mice (KLH conjugated) 3 times at 2-week intervals (120 μg/60 μl×1 site/administration). Type II collagen and CFA (complete Freund's adjuvant) were administered at 28 days from the first vaccine administration, and Type II collagen and IFA (incomplete Freund's adjuvant) were administered at 42 days from the first vaccine administration, to induce arthritis. Thereafter, the level of arthritis was observed 3 times per week and scored. The administration plan is shown in FIG. 22(A).

Experiment 8

DBA/1 mouse
H17 (human IL-17A1 epitope) group: 3 mice
AF4 (human IL-17A4 epitope) group: 3 mice
AF5 (human IL-17A2 epitope) group: 3 mice
Control (KLH) group: 4 mice
Collagen(−) group: 3 mice
Clinical Score The clinical score of arthritis of DBA/1 mouse described in Experiment 8 was examined. It was found that the vaccine group consisting of human IL-17A1 epitope, human IL-17A2 epitope or human IL-17A4 epitope shows a suppressive effect on the onset and progression of arthritis (FIG. 22(B)).

From the above results, human IL-17A vaccine showed a suppressive effect on arthritis in arthritis model mouse caused by Type II collagen.

Example 9

In Vitro Neutralization Activity on IL-17A

The secretion amount of IL-6 when recombinant human IL-17A was added to normal human dermal fibroblast (NHDF) in a medium was measured by ELISA. As a result, addition of IL-17A promoted secretion of IL-16 (IL-17 only). However, when IgG purified from antiserum of a mouse immunized with a vaccine containing a peptide consisting of human IL-17A1 epitope was simultaneously added with IL-17A, secretion of IL-6 was suppressed (IL-17+antisera). In addition, when IgG purified from antiserum of a non-immunized mouse was simultaneously added with IL-17A, secretion of IL-6 was scarcely suppressed (IL-17+ control sera). These results are shown in FIG. 23.

From the above results, an antibody obtained by immunization with a vaccine containing a peptide consisting of human IL-17A1 epitope suppressed secretion of IL-6 from cultured cells in vitro. Therefore, the antibody was suggested to have a neutralization action on IL-17A activity, and suggested to be effective for the treatment effect of diseases involving IL-17A in the aggravation.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

As described in detail in the above, the vaccine of the present invention increases the antibody titer to IL-17A, can be used for not only SLE but also other diseases involving IL-17A in the aggravation of pathology, such as rheumatoid arthritis, inflammatory bowel disease, cancer, psoriasis, multiple sclerosis, arteriosclerosis and the like, and can greatly contribute to the treatment and the like of these diseases.

This application is based on patent application No. 2013-273133 filed in Japan (filing date: Dec. 27, 2013), the contents of which are incorporated in full herein.

The invention claimed is:

1. A method for suppressing progression of a disease involving IL-17A as an aggravation factor or treating a disease involving IL-17A as an aggravation factor comprising administering a polypeptide consisting of the amino acid sequence shown in SEQ ID NO: 1.

2. The method according to claim 1, wherein the method further comprises administering a carrier protein and/or an adjuvant.

3. The method according to claim 1, wherein the method further comprises administering a carrier protein selected from the group consisting of a bovine serum albumin (BSA), rabbit serum albumin (RSA), ovalbumin (OVA), keyhole-limpet hemocyanin (KLH), thyroglobulin (TG), and immunoglobulin.

4. The method according to claim 3, wherein the carrier protein is a BSA.

5. The method according to claim 3, wherein the carrier protein is a RSA.

6. The method according to claim 3, wherein the carrier protein is a OVA.

7. The method according to claim 3, wherein the carrier protein is a KLH.

8. The method according to claim 3, wherein the carrier protein is a TG.

9. The method according to claim 3, wherein the carrier protein is an immunoglobulin.

10. The method according to claim 1, wherein the disease involving IL-17A as an aggravation factor is selected from the group consisting of systemic lupus erythematosus (SLE), inflammatory bowel disease, rheumatoid arthritis, tumor, psoriasis, and multiple sclerosis.

11. The method according to claim 1, comprising wherein the disease involving IL-17A as an aggravation factor is selected from the group consisting of SLE, inflammatory bowel disease, rheumatoid arthritis, colon cancer, and lung cancer.

12. The method according to claim 1, wherein the disease involving IL-17A as an aggravation factor is SLE.

13. The method according to claim 1, wherein the disease involving IL-17A as an aggravation factor is inflammatory bowel disease.

14. The method according to claim 1, wherein the disease involving IL-17A as an aggravation factor is rheumatoid arthritis.

15. The method according to claim 1, wherein the disease involving IL-17A as an aggravation factor is a tumor.

16. The method according to claim 1, wherein the disease involving IL-17A as an aggravation factor is psoriasis.

17. The method according to claim 1, wherein the disease involving IL-17A as an aggravation factor is multiple sclerosis.

18. The method according to claim 1, wherein the disease involving IL-17A as an aggravation factor is colon cancer.

19. The method according to claim 1, wherein the disease involving IL-17A as an aggravation factor is lung cancer.

* * * * *

SEQUENCE LISTING

```
<160> NUMBER OF SEQ ID NOS: 17

<210> SEQ ID NO 1
<211> LENGTH: 8
<212> TYPE: PRT
<213> ORGANISM: Homo sapiens

<400> SEQUENCE: 1

Arg Ser Ser Asp Tyr Tyr Asn Arg
1               5

<210> SEQ ID NO 2
<211> LENGTH: 24
<212> TYPE: DNA
<213> ORGANISM: Homo sapiens

<400> SEQUENCE: 2
aggtcctcag attactacaa ccga                                           24

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
gccatggata tcgatcctta taaagaattc ggagc                               35

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
ggcctctcac taacattgag attcccgaga ttgaga                              36

<210> SEQ ID NO 5
<211> LENGTH: 8
<212> TYPE: PRT
<213> ORGANISM: Mus musculus

<400> SEQUENCE: 5
```

```
Arg Pro Ser Asp Tyr Leu Asn Arg
1               5

<210> SEQ ID NO 6
<211> LENGTH: 24
<212> TYPE: DNA
<213> ORGANISM: Mus musculus

<400> SEQUENCE: 6
cggccctccg actacctgaa ccgg                                            24

<210> SEQ ID NO 7
<211> LENGTH: 7
<212> TYPE: PRT
<213> ORGANISM: Mus musculus

<400> SEQUENCE: 7

Asp His His Met Asn Ser Val
1               5

<210> SEQ ID NO 8
<211> LENGTH: 17
<212> TYPE: PRT
<213> ORGANISM: Homo sapiens

<400> SEQUENCE: 8

Ala Asp Gly Asn Val Asp Tyr His Met Asn Ser Val Pro Ile Gln Gln
1               5                   10                  15

Glu

<210> SEQ ID NO 9
<211> LENGTH: 14
<212> TYPE: PRT
<213> ORGANISM: Homo sapiens

<400> SEQUENCE: 9

Leu Arg Arg Glu Pro Pro His Cys Pro Asn Ser Phe Arg Leu
1               5                   10

<210> SEQ ID NO 10
<211> LENGTH: 17
<212> TYPE: PRT
<213> ORGANISM: Mus musculus

<400> SEQUENCE: 10

Ala Glu Gly Lys Leu Asp His His Met Asn Ser Val Leu Ile Gln Gln
1               5                   10                  15

Glu

<210> SEQ ID NO 11
<211> LENGTH: 5
<212> TYPE: PRT
<213> ORGANISM: Homo sapiens

<400> SEQUENCE: 11

Ser Asp Tyr Tyr Asn
1               5

<210> SEQ ID NO 12
<211> LENGTH: 4
<212> TYPE: PRT
<213> ORGANISM: Homo sapiens

<400> SEQUENCE: 12
```

```
Ser Asp Tyr Tyr
1

<210> SEQ ID NO 13
<211> LENGTH: 51
<212> TYPE: DNA
<213> ORGANISM: Homo sapiens

<400> SEQUENCE: 13
gctgatggga acgtggacta ccacatgaac tctgtcccca tccagcaaga g        51

<210> SEQ ID NO 14
<211> LENGTH: 51
<212> TYPE: DNA
<213> ORGANISM: Mus musculus

<400> SEQUENCE: 14
gcggagggaa agctggacca ccacatgaat tctgttctca tccagcaaga g        51

<210> SEQ ID NO 15
<211> LENGTH: 15
<212> TYPE: DNA
<213> ORGANISM: Homo sapiens

<400> SEQUENCE: 15
tcagattact acaac                                                 15

<210> SEQ ID NO 16
<211> LENGTH: 12
<212> TYPE: DNA
<213> ORGANISM: Homo sapiens

<400> SEQUENCE: 16
tcagattact ac                                                    12

<210> SEQ ID NO 17
<211> LENGTH: 570
<212> TYPE: DNA
<213> ORGANISM: Hepatitis B virus

<400> SEQUENCE: 17
atggatatcg atccttataa agaattcgga gctactgtgg agttactctc gtttctcccg     60
agtgacttct ttccttcagt acgagacctt ctggataccg ccagcgcgct gtatcgggaa    120
gccttggagt ctcctgagca ctgcagccct caccatactg ccctcaggca agcaattctt    180
tgctgggggg agctcatgac tctggccacg tgggtgggtg ttaacttgga agatccagct    240
atcactggtg ctactagcag ggacctggta gtcagttatg tcaacactaa tatgggttta    300
aagttcaggc aactcttgtg gtttcacatt agctgcctca ctttcggccg agaaacagtt    360
atagaatatt tggtgtcttt cggagtgtgg atccgcactc ctccagctta taggcctccg    420
aatgccccta tcctgtcgac actcccggag actactgttg ttagacgtcg aggcaggtca    480
cctagaagaa gaactccttc gcctcgcagg cgaaggtctc aatcgccgcg gcgccgaaga    540
tctcaatctc gggaatctca atgttagtga                                    570
```